United States Patent [19]

Forte

[11] Patent Number: 5,800,552

[45] Date of Patent: Sep. 1, 1998

[54] MECHANICALLY LINKED HINGED TOTAL KNEE PROSTHESIS

[76] Inventor: Mark R. Forte, 11 Oak La., Pine Brook, N.J. 07058

[21] Appl. No.: 327,092

[22] Filed: Oct. 21, 1994

Related U.S. Application Data

[60] Division of Ser. No. 854,225, Mar. 20, 1992, Pat. No. 5,358,527, which is a continuation-in-part of Ser. No. 673,790, Mar. 22, 1991, Pat. No. 5,236,461.

[51] Int. Cl.$^6$ .................................................. A61F 2/38
[52] U.S. Cl. ............................................................ 623/20
[58] Field of Search .................................. 623/16, 18, 20

[56] References Cited

U.S. PATENT DOCUMENTS

| | | |
|---|---|---|
| 3,728,742 | 4/1973 | Averill et al. . |
| 3,774,244 | 11/1973 | Walker . |
| 3,837,009 | 9/1974 | Walker . |
| 3,996,624 | 12/1976 | Noiles . |
| 4,081,866 | 4/1978 | Upshaw et al. . |
| 4,136,405 | 1/1979 | Pastrick et al. . |
| 4,207,627 | 6/1980 | Cloutier . |
| 4,209,861 | 7/1980 | Walker et al. . |
| 4,213,209 | 7/1980 | Insall et al. . |
| 4,216,549 | 8/1980 | Hillberry et al. ..................... 623/20 |
| 4,298,992 | 11/1981 | Burstein et al. . |
| 4,865,606 | 9/1989 | Rehder ................................. 623/20 |
| 4,888,021 | 12/1989 | Forte et al. . |
| 4,892,547 | 1/1990 | Brown . |
| 4,959,071 | 9/1990 | Brown et al. . |

FOREIGN PATENT DOCUMENTS

| | | | |
|---|---|---|---|
| 2566657 | 1/1986 | France ................................. 623/20 |
| 2901009 | 7/1980 | Germany ............................. 623/20 |

*Primary Examiner*—David H. Willse
*Attorney, Agent, or Firm*—Klauber & Jackson

[57] ABSTRACT

A resurfacing type of total knee prosthesis is disclosed which also provides a posterior stabilization function over the entire range of flexion. The knee prosthesis provides primary or supplementary posterior stabilization of the reconstructed knee joint by means of a unique mechanical cam/follower mechanism, which is integrated within the medial and lateral distal condyles of the femoral component to provide functional compensation for lost, resected or incompetent posterior cruciate ligaments or to work in conjunction with surgically retained viable or questionably viable cruciate ligament structures of the reconstructed knee joint. The invention extends to prostheses including a hinge connection that defines a posterior stabilization construction separate from that defined by the condyles. One embodiment of the invention extends individually to the posterior stabilizing hinge assembly.

16 Claims, 13 Drawing Sheets

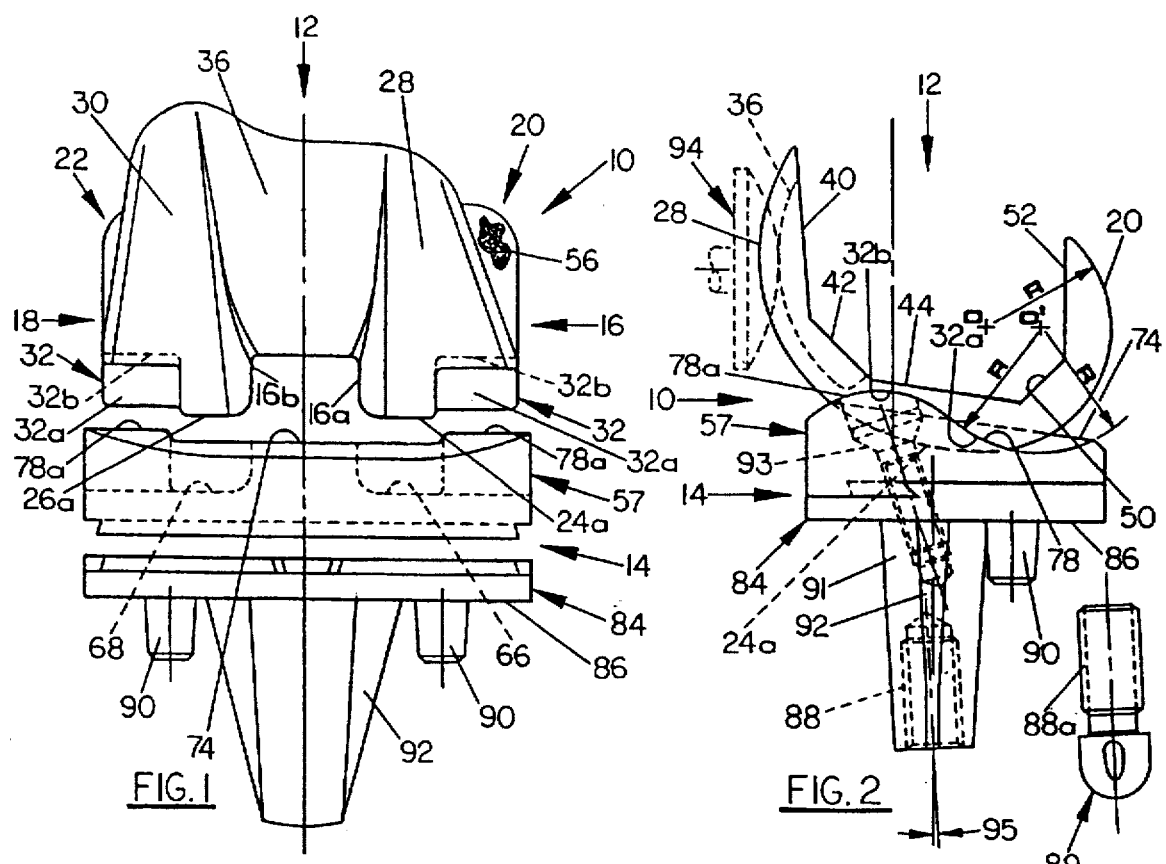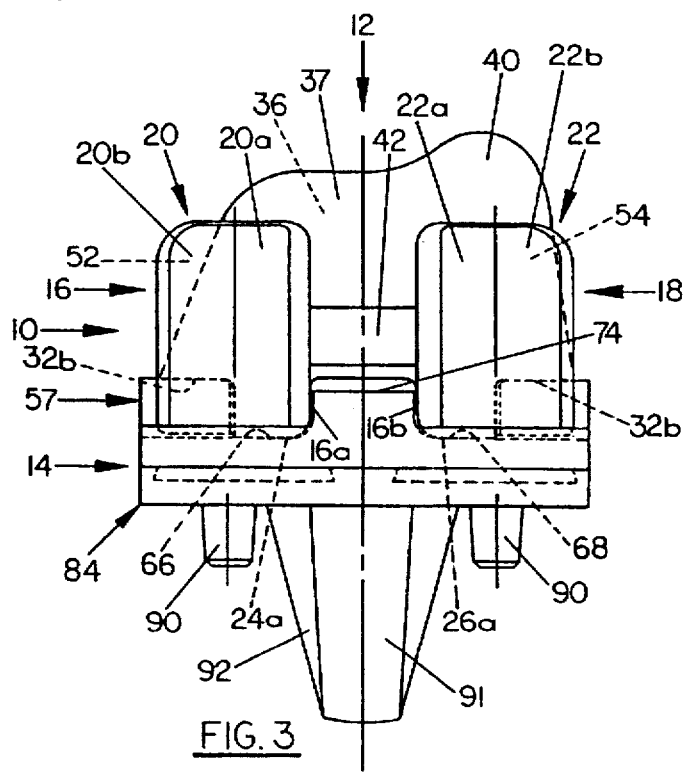

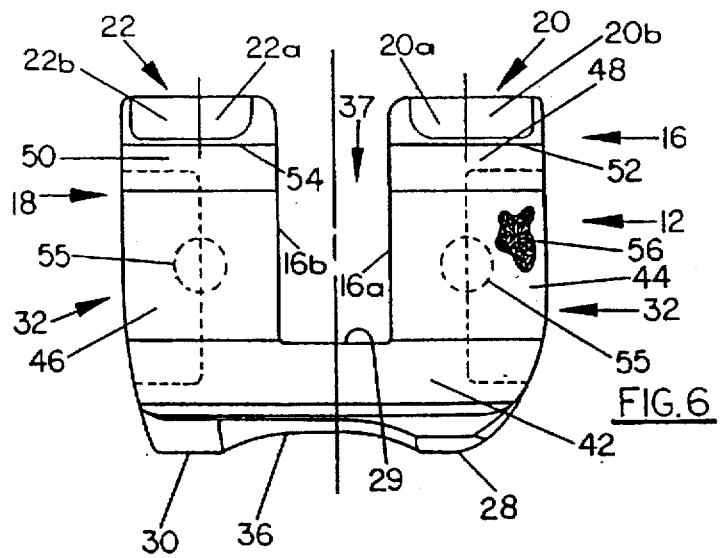
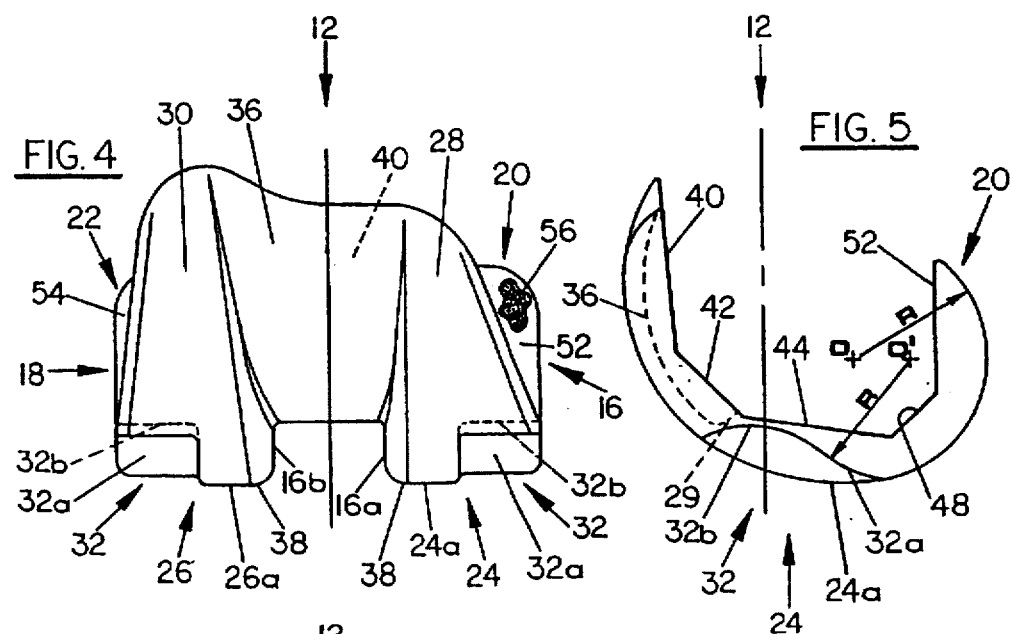
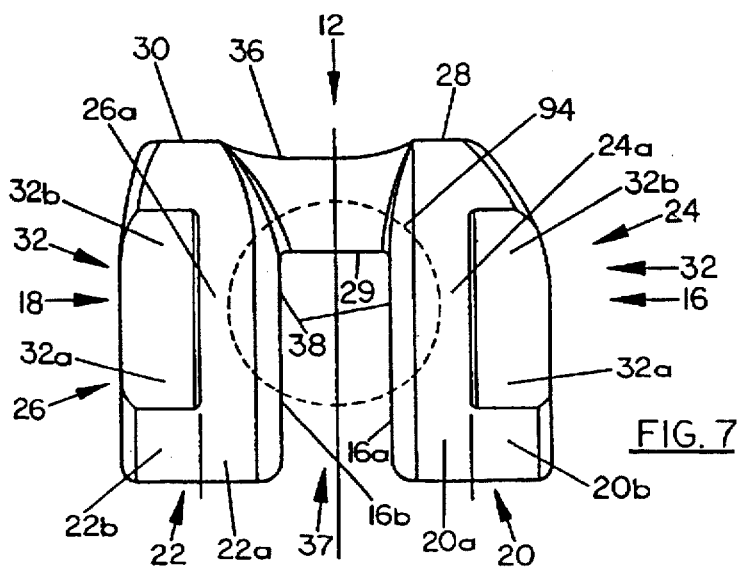

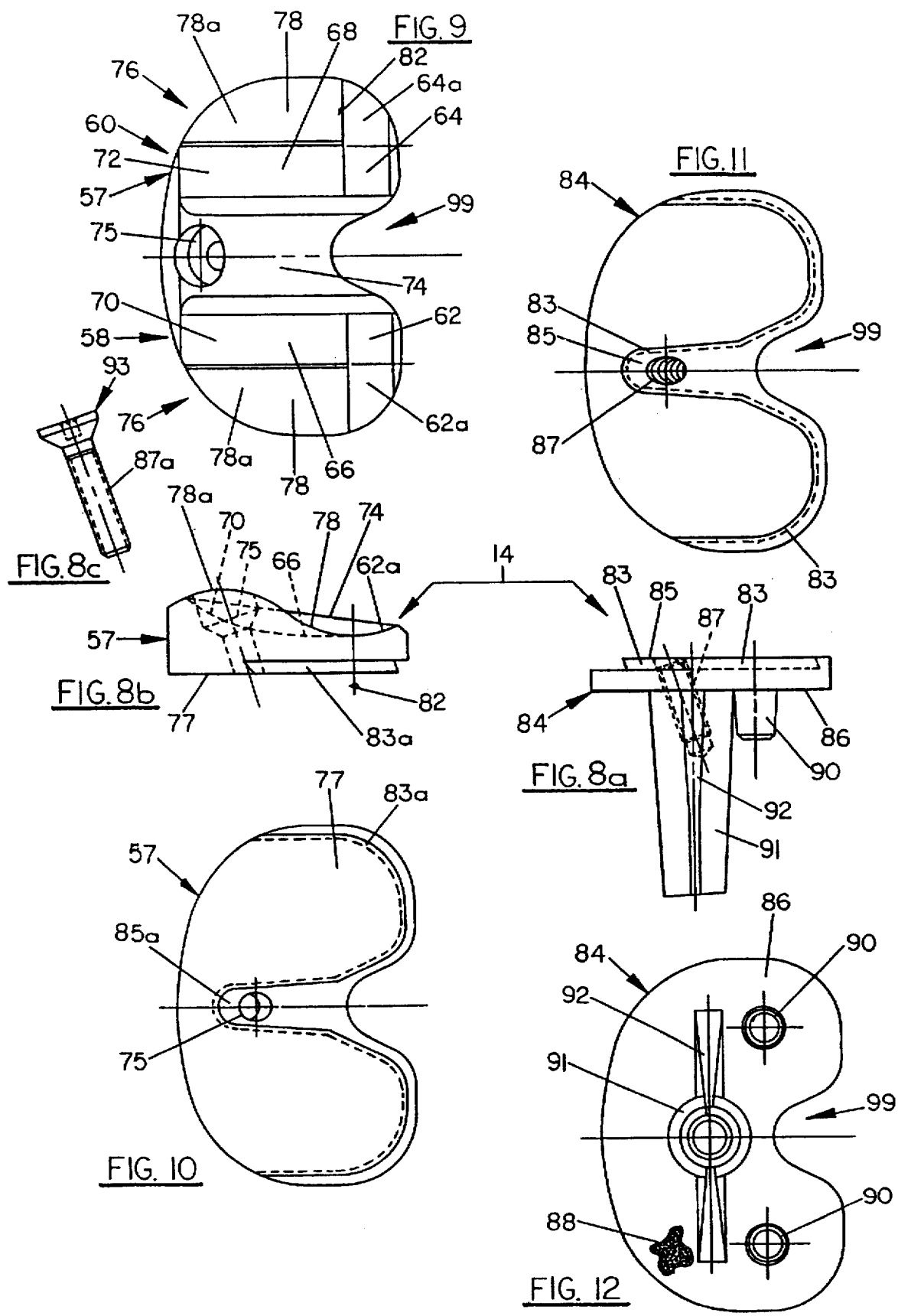

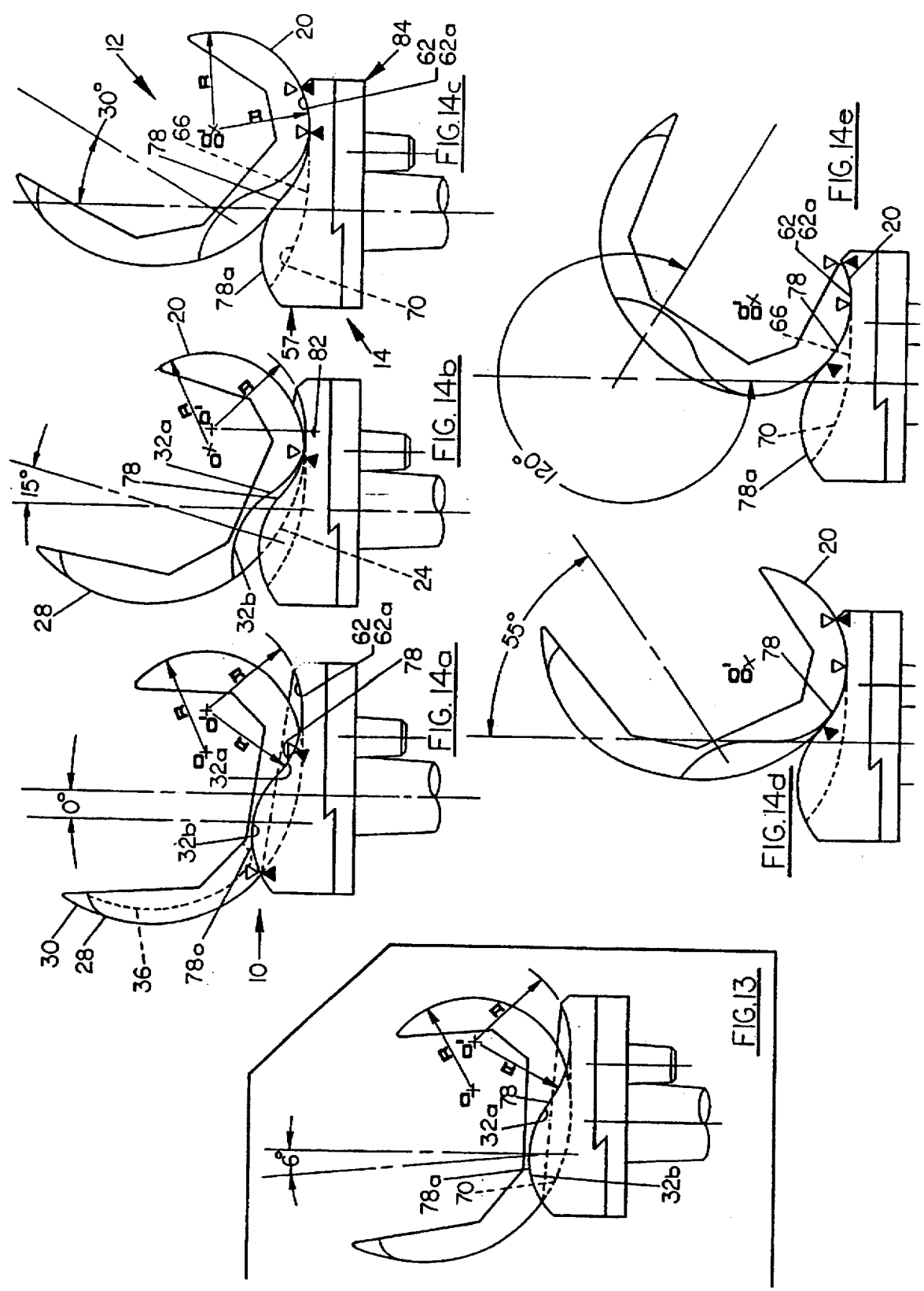

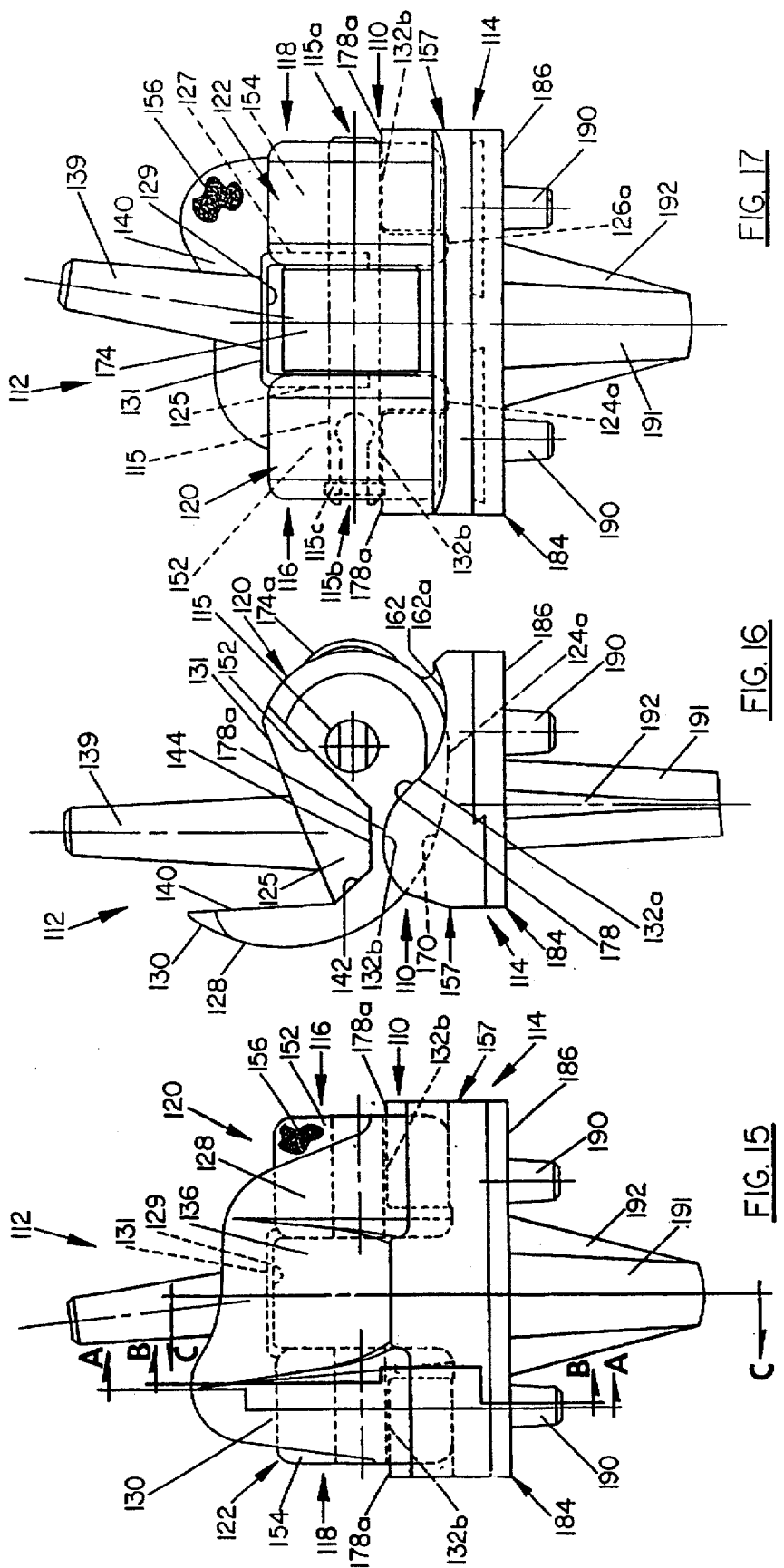

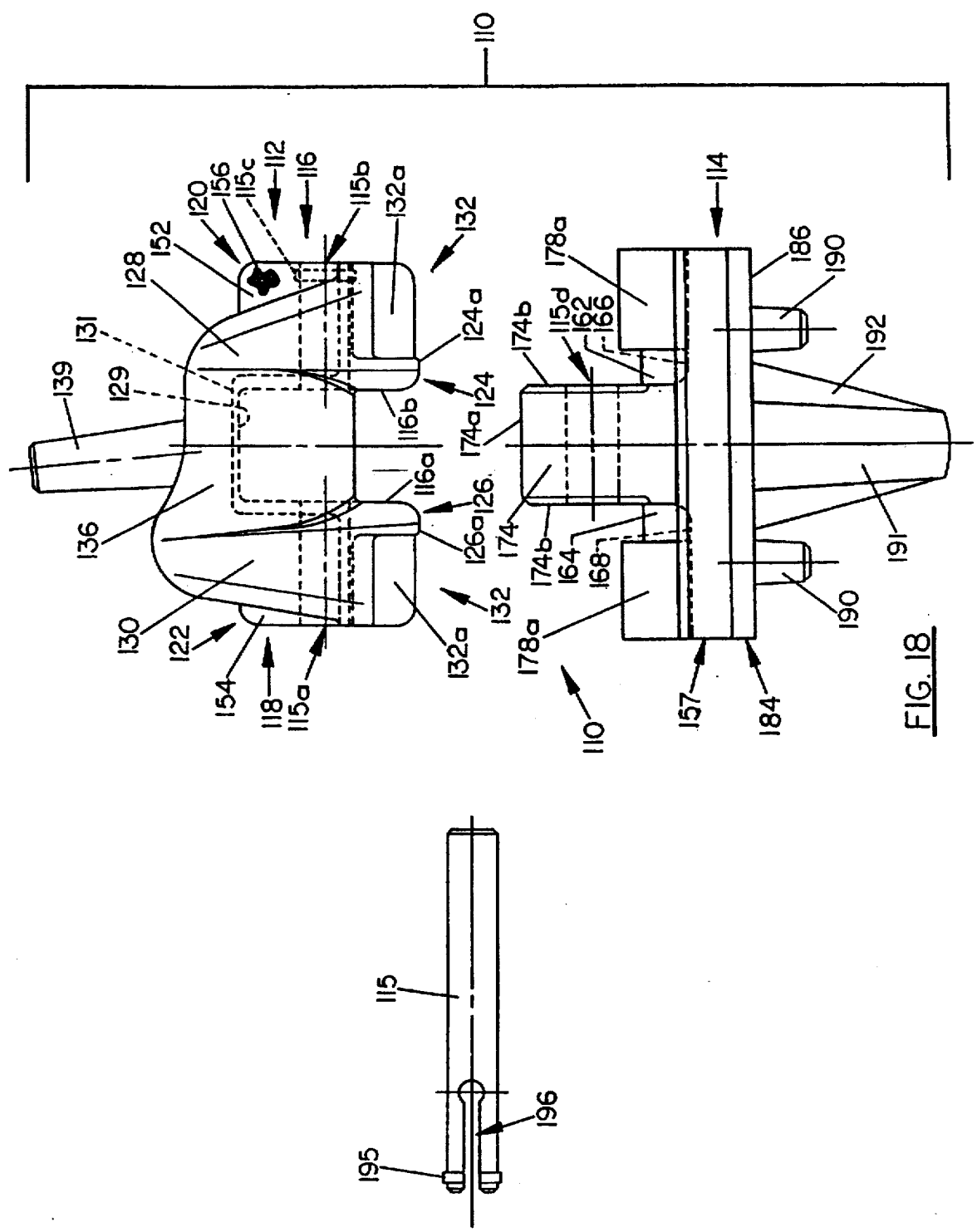

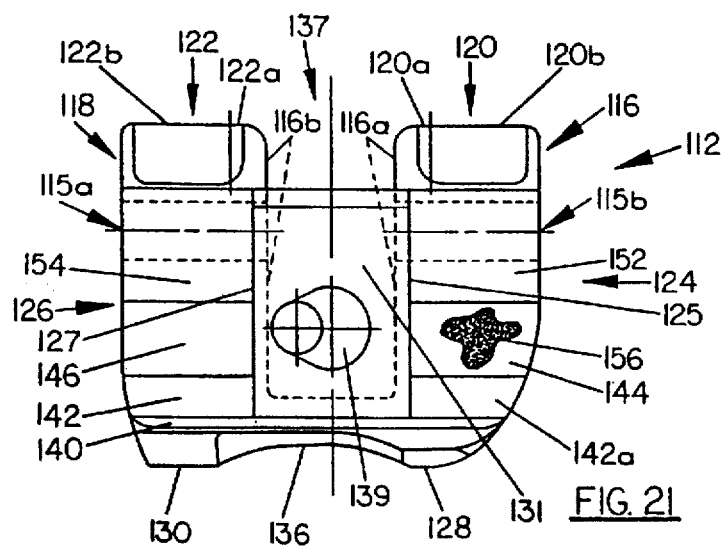
FIG. 21
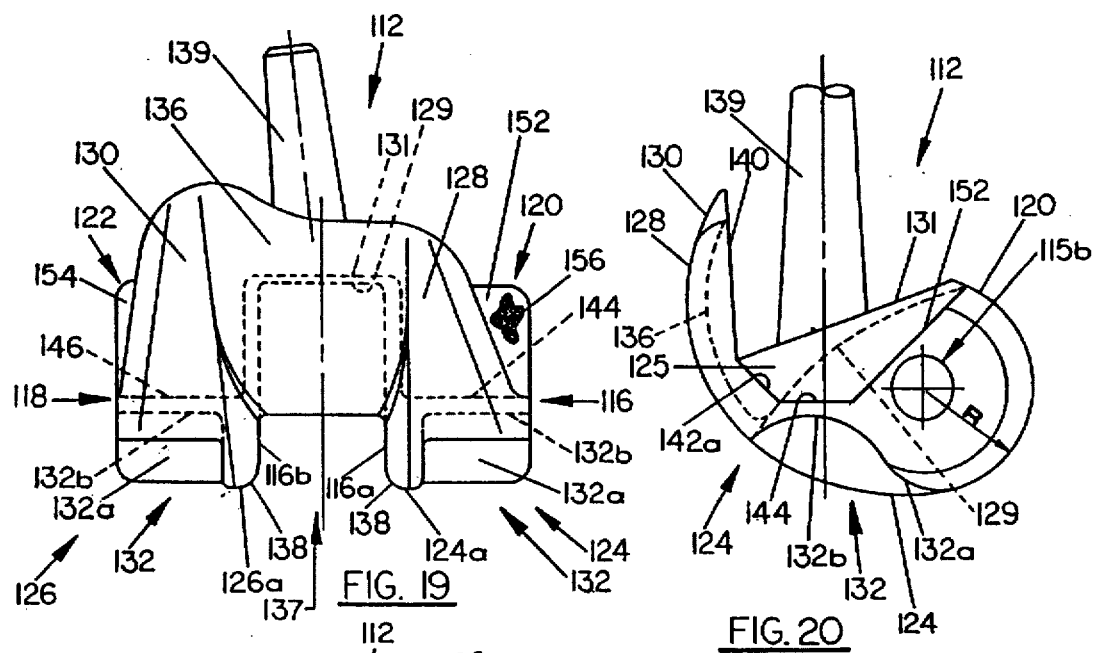
FIG. 19
FIG. 20
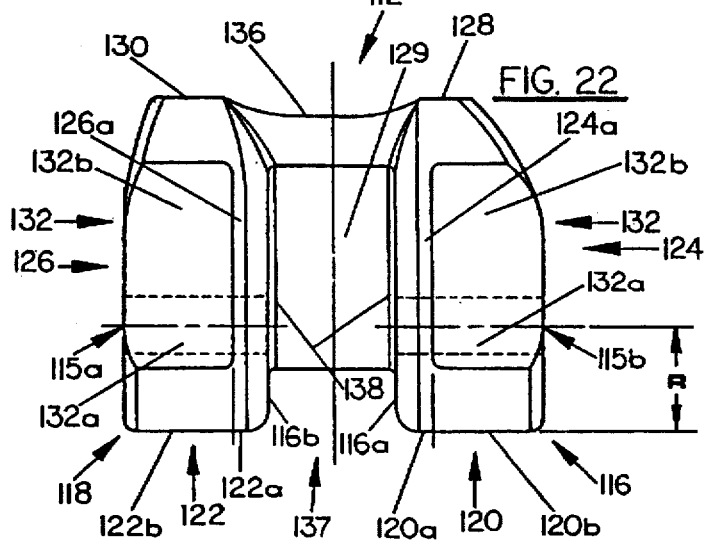
FIG. 22

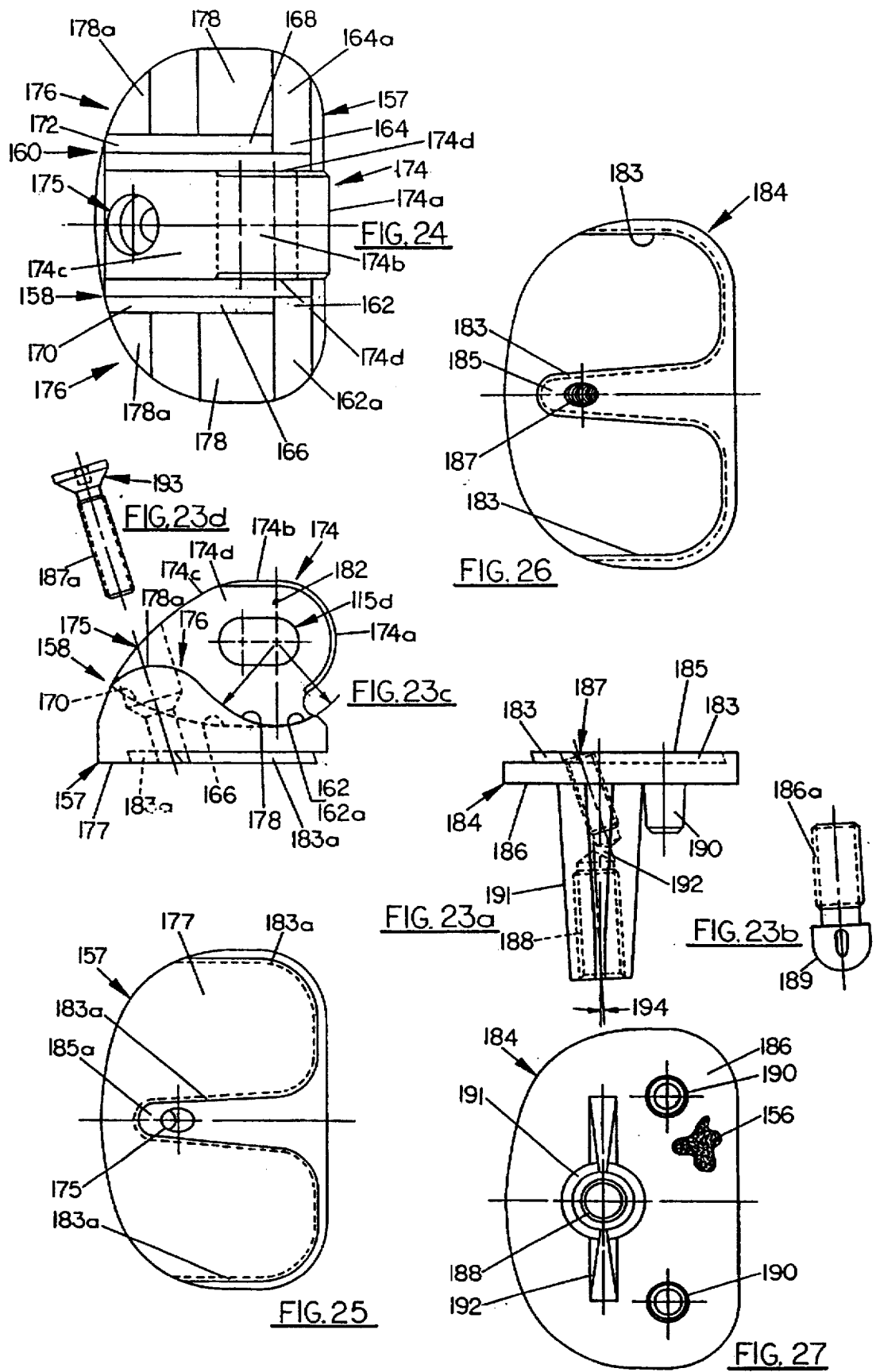

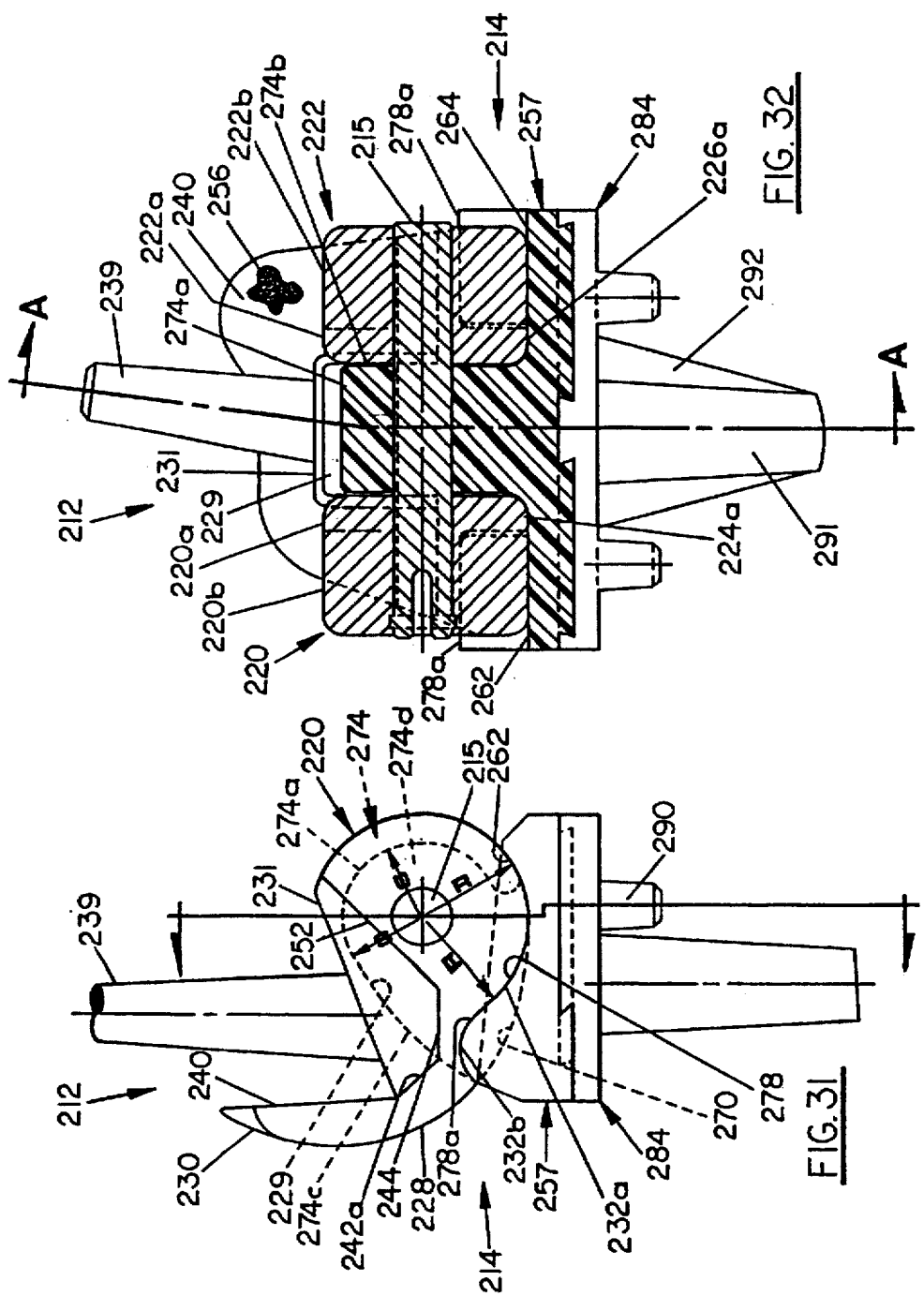

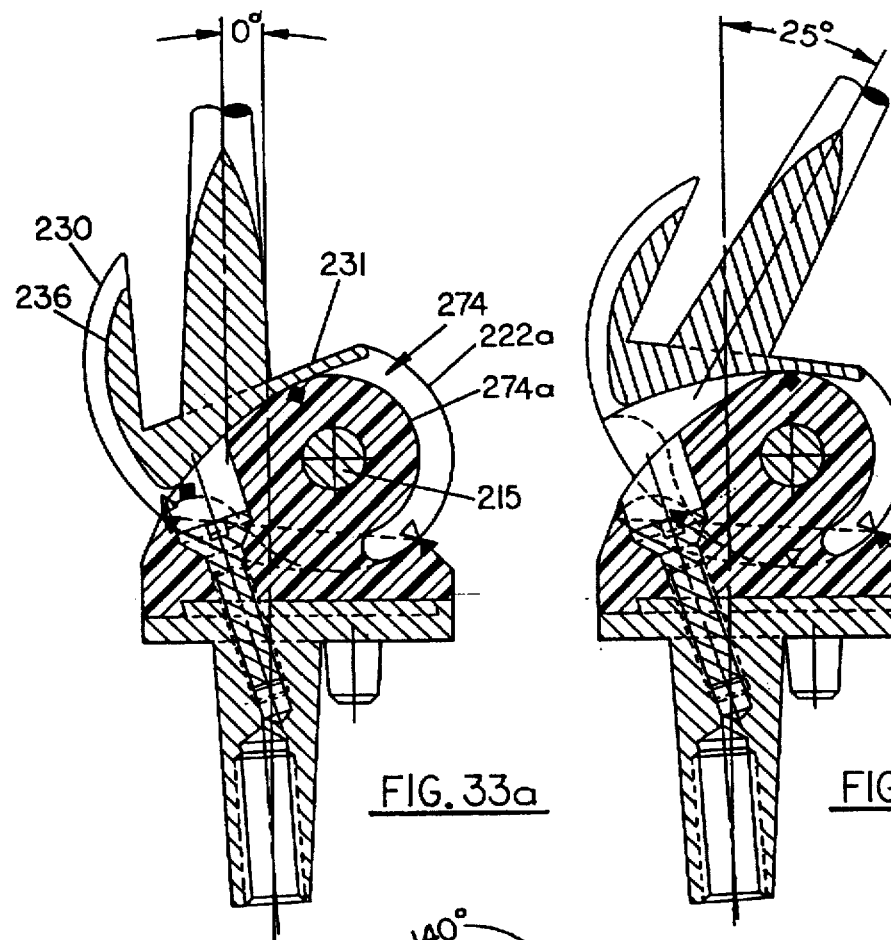
FIG. 33a
FIG. 33b
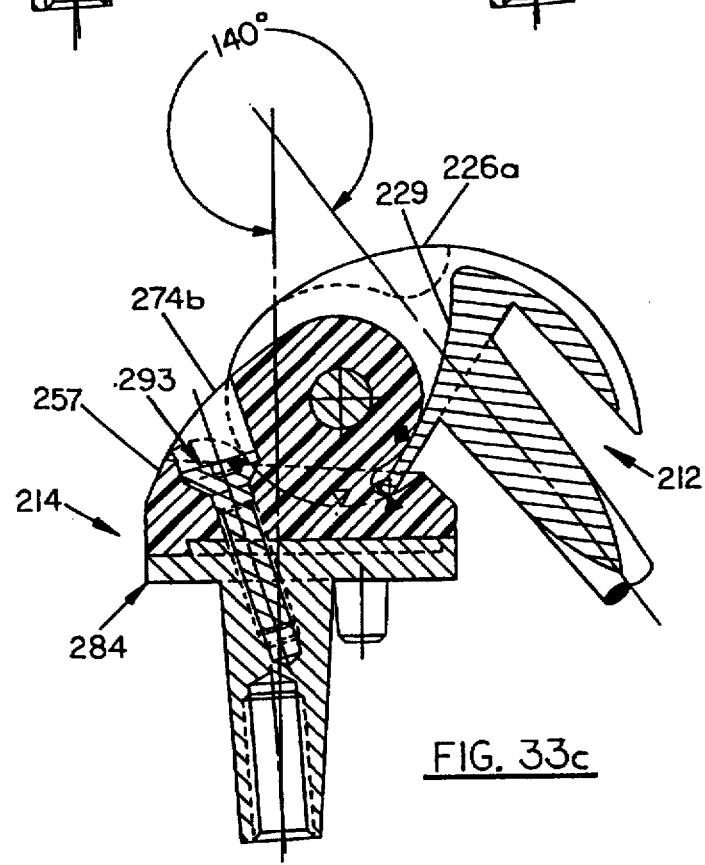
FIG. 33c

MECHANICALLY LINKED HINGED TOTAL KNEE PROSTHESIS

CROSS-REFERENCE TO RELATED APPLICATION

This is a division of application Ser. No. 07/854,225, filed Mar. 20, 1992, now U.S. Pat. No. 5,358,527, which is a continuation-in-part of application Ser. No. 07/673,790, filed Mar. 22, 1991, now U.S. Pat. No. 5,236,461. Priority under 35 U.S.C. §120 is claimed as to the above earlier filed Application, and the disclosure thereof is incorporated herein by reference.

BACKGROUND OF THE INVENTION

The present invention relates generally to knee prostheses and, more particularly, to a resurfacing type of total knee prosthesis which also provides a posterior stabilization function over the entire range of flexion, and which in one embodiment includes a hinged construction.

Known total knee prostheses can essentially be classified into three basic categories. In the first category, the articular surface of the distal femur and proximal tibia are "resurfaced" with respective metal and plastic condylar-type articular bearing components. These knee prostheses provide adequate rotational and translational freedom and require minimal bone resection to accommodate the components within the boundaries of the available joint space. The patella-femoral joint may also be resurfaced by a third prosthetic component, as well. The femoral, tibial and patella prosthetic resurfacing components are affixed to respective, surgically prepared adjacent bone structure by a cementing or by a biological bone ingrowth fixation means.

The femoral component is a metallic alloy construction (cobalt-chrome alloy or 6A14V titanium alloy) and provides medial and lateral condylar bearing surfaces of multi-radius design of similar shape and geometry as the natural distal femur or femoral-side of the knee joint. The tibial component can be made entirely of plastic (UHMWPE: ultra high molecular weight polyethylene) or can be comprised of a metallic base component, distally, and an interlocking plastic (UHMWPE) component, proximally. The plastic tibial plateau bearing surfaces are of concave multi-radius geometry to more or less match the articular geometry of the mating femoral condyles, depending upon the desired design mechanics of primary femoro-tibial motion, e.g. the flexion-extension mode-including posterior rollback and the secondary rotational and translational articular motions. In the resurfacing type of total knee prostheses both the femoral and tibial components are positioned on the respective side of the knee joint and are not mechanically connected or linked together, as in the case of constrained or hinged type of knee prostheses, which constitutes another or second category of total knee prostheses.

Additionally, in resurfacing types of total knee prostheses according to the first category, as previously stated, the tibial plateau bearing surface geometry can assume a variety of configurations, depending upon the desired extent of articular contact congruency and associated translational (medial-lateral and anterior-posterior) and rotational (axial and varus-valgus) secondary femoro-tibial motions. These various secondary motions allow the resurfaced knee to function in a natural-like biomechanical manner in conjunction with the surrounding ligamentous and muscle structures about the knee joint. The viable soft tissue structures functionally maintain the femoral and tibial bearing surfaces in contact, provide the necessary levels of constraining force to achieve knee joint stability, and decelerate the principal motion in flexion-extension and secondary motions, such as axial rotation, etc. in a controlled manner. Additionally, this functional interaction between the surrounding tissue structures and the implanted knee prosthesis minimizes abrupt motion stoppage or impact loading of properly designed prosthetic articular surfaces, and thus prevents overstressing at the component fixation interface. Examples of resurfacing types of total knee prosthetic devices are disclosed in U.S. Pat. No. 3,774,244 to Walker; U.S. Pat. No. 3,728,742 to Averill et al.; U.S. Pat. No. 4,081,866 to Upshaw et al. and U.S. Pat. No. 4,207,627 to Cloutier.

On the other hand, the mechanically linked, constrained or hinged type of knee prosthesis according to the second category provides a fixed fulcrum flexion-extension capability. Some of these devices are fully constrained in axial rotation, while others provide either partially constrained or unconstrained axial rotational freedom. The "hinged knee", therefore, is usually surgically indicated in selected cases where the surrounding soft tissue structures are grossly degenerated and incapable of providing functionally acceptable knee joint stability. Examples of this type of total knee prosthetic device are disclosed in U.S. Pat. No. 3,996,624 to Noiles; U.S. Pat. No. 3,837,009 to Walker; and U.S. Pat. No. 4,136,405 to Pastrick et al.

In clinical situations where prosthetic knee joint reconstruction is surgically indicated in the presence of compromised posterior (tibia-to-femur) stability, that is, due to absent or incompetent posterior cruciate ligament structures, a posterior-stabilized total knee device can be utilized. This type of device constitutes the third category of total knee prosthetic devices. The posterior-stabilized total knee device essentially incorporates all of the functional features of the first category, that is, the resurfacing condylar-type of knee prostheses, in addition to incorporating a mechanical cam/follower mechanism for providing posterior (tibia-to-femur) constraint. The cam/follower mechanism is almost universally positioned within the intercondylar space of the femoral component and provides substitutional posterior constraint, as a predesigned compensation feature for lost posterior cruciate function or for compromised posterior knee stability. Thus, the possibility of anterior dislocation of the femur is reduced.

Additionally, the cam/follower mechanism is generally positioned between the anterior and posterior femoral condyles and dimensionally spans the femoro-tibial joint space; protruding into the sector of intercondylar bone within the distal femur; thus, occupying the sector within the knee joint where the cruciate ligaments are anatomically located. Surgical selection of a posterior stabilized type of knee prosthesis, therefore, generally predisposes the use of this type device exclusively in clinical situations where the natural posterior (and anterior) cruciate ligament structures of the knee joint are absent or sacrificed.

The cam portion of the cam/follower mechanism of the posterior stabilized device generally includes a convex lobe-shaped surface, integrally machined or cast within a box-like structure known as the "stabilizer box", which in turn, is integrally located between the medial and lateral condyle runners of the femoral component and positioned between the anterior and posterior condyles. The cam surface is generally formed within the posterior wall portion of the stabilizer box and is bounded by the superior wall on the top, the medial and lateral wall portions on the sides and the anterior wall portion at the front. The stabilizer box structure, thus formed, occupies a significant envelope, relative to the overall dimensions of the femoral component and therefore, requires a substantial resection of viable bone to allow its accommodation within the intercondylar sector of the distal femur.

The articular surface of the posteriorly positioned and anteriorly oriented convex cam member is generally precisely ground and highly polished. The convex cam articulates with the anteriorly positioned and posteriorly oriented follower member, as the knee undergoes femoro-tibial flexion and extension articulation. The mating follower surface is machined integral within the ultra-high molecular weight polyethylene (UHMWPE) tibial plateau bearing component. The follower member usually consists of a relatively concave articular surface located on the posterior side of an upwardly extending post-like structure, which is positioned between the concave medial and lateral tibial plateau bearing surfaces.

The post-like structure of the follower member extends upward and generally is of sufficient over-all height to span the joint space; thus, protruding into and occupying an appropriate position within the stabilizer box portion for mating with the cam member of the cam/follower mechanism. The cam/follower mechanism, therefore, not only functionally compensates for lost posterior cruciate function, but also occupies essentially the same intercondylar position within the knee joint; thus requiring that the posterior (and anterior) cruciate ligament structures be either absent or sacrificed.

The resultant action of the contacting cam/follower mechanism, thus described, provides posterior stabilization or constraint of the tibial component, relative to the femoral component, generally from about mid-range to full range of flexion. Within this limited range, therefore, the posterior stabilizing mechanism essentially simulates the functional contribution of the natural posterior cruciate ligaments attached between the anterior femoral and posterior tibial aspects of the knee joint. Additionally, since the cam/follower surface geometry is generally non-congruent, the mechanism can be designed to produce posterior femoro-tibial rollback, simulating the biomechanical kinematic displacement characteristics of the natural knee joint.

Examples of posterior-stabilized total knee prostheses of the type just described are disclosed in U.S. Pat. No. 4,209,861 to Walker; U.S. Pat. No. 4,298,992 to Burstein et al.; U.S. Pat. No. 4,213,209 to Insall et al; and U.S. Pat. No. 4,888,021 to Forte et al. Each of the devices described in the above patents incorporates a UHMWPE tibial plateau bearing component with a pair of medial and lateral concave bearing surfaces, and a metal alloy femoral component with mating multi-radius condylar runners which ride on the bearing surfaces. In all cases prosthesis surface geometries approximate the articular surfaces of the natural knee. The articulation of the femoral condyles with the tibial plateau bearing surfaces allows primary femoro-tibial flexion and extension, and secondary motions of axial and varus-valgus rotations and anterior-posterior and medial-lateral translations. The knee joint reaction forces during primary or secondary motion are principally supported by the tibial bearing surfaces, and to some extent by the cam/follower surfaces, and are transferred to the underlying fixation interfaces and adjacent supportive bone structures.

Additionally, the above referenced designs incorporate a UHMWPE tibial bearing component with an upwardly extending post-like follower structure, which is positioned between the plateau bearing surfaces, slightly anterior of the component mid-line. The generally concave follower surface is integrally machined on the posterior side of the central post structure. With the femoral and tibial knee components in a normally reduced, surgically implanted position, the upwardly extending tibial post protrudes into the stabilizer box structure located within the intercondylar space of the femoral component. Posterior tibial constraint is achieved when the posteriorly oriented concave face of the follower contacts the generally anteriorly oriented convex lobe surface of the cam.

Both cam/follower articulation and femoro-tibial articulation occur concurrently during knee flexion-extension. The commencement of cam/follower contact, and hence, commencement of posterior stabilization occurs on or about mid-flexion range for the devices described in U.S. Pat. Nos. 4,213,209 and 4,298,992, and near the onset of knee flexion for the devices described in U.S. Pat. Nos. 4,888,021 and 4,209,861. It should be noted that however, that there are forces acting over the entire range of motion of the patented devices that are not accounted for in the patent disclosures.

In each of the above devices, the existence of a relatively large stabilizer box at the mid-portion of the femoral component requires resection of a significant block of viable intercondylar bone to accommodate the implantation of the femoral component prosthetic device. Moreover, additional surgical instrumentation is required and the surgical procedure is somewhat more complicated compared to a conventional condylar-type knee resurfacing device. Additionally, the cam/follower mechanism of the referenced devices essentially occupies the same intercondylar position within the knee joint as the cruciate ligaments; therefore, the use of these posterior stabilized knee prostheses are usually surgically indicated in those clinical situations where the cruciate ligaments are either absent or incompetent, or such ligaments must be intentionally sacrificed for these prostheses to be implanted. In other words, these posterior stabilized knee prostheses generally can not be effectively employed to function in conjunction with retained, viable posterior (and anterior) cruciate ligament structures because of space limitations and impending destructive interference with the cam/follower structure.

Furthermore, in each instance, the stabilizer box member has prominent (high profile) medial and lateral side walls and also, anterior and posterior walls. These bounding surfaces can inadvertently contact the upwardly extending tibial post during severe excursions of secondary knee motion, that is, during axial and varus-valgus rotations and medial-lateral translation; hence, can function to constrain these secondary movements within certain limitations, commensurate with design dimensional clearance. While these devices have been effective in constraining these types of motion excursions and therefore, effective in providing a high degree of controlled femoro-tibial stability, the resulting force reactions occurring between the stabilizer box surfaces and tibial post can produce periodic and severe (moment and torque) loading at the tibial component fixation sub-structure interfaces, which can cause complications related to component loosening.

Another type of posterior stabilized knee prosthesis is described in U.S. Pat. Nos. 4,892,547 and 4,959,071 to Brown. These designs incorporate a cam/follower mechanism having a low profile and require no resection penalty associated with the accommodation of a protruding stabilizer box structure. The heights of the tibial follower post (eminence) and the femoral cam members are no greater than the thickness of the distal and posterior condyles of the femoral component. The required femoral resections are thus identical to those of a conventional resurfacing condylar type of knee prosthesis of similar size and geometric design.

The devices disclosed in these patents however, suffer from other disadvantages. First, although the relatively short extending tibial post is located between the plateau bearing surfaces, the cam member is integrally incorporated at a high position, between the posterior condyles of the femoral component. These knee devices are, therefore, described as "partially stabilized" knee joint prostheses; since, the cam/follower mechanism only comes into contact after flexion of approximately 40 degrees has occurred and continues until full flexion is attained. Thus, there is no posterior tibia-to-femur constraint of the reconstructed knee joint from the outset of flexion to approximately 40 degrees flexion. In this regard, these knee devices are functionally similar to other posterior stabilized knee devices, such as those disclosed in U.S. Pat. Nos. 4,213,209 and 4,298,992, previously discussed. These patents, therefore, do not take into account the forces acting over the entire range of motion of the knee joint.

Further with respect to the referenced patents to Brown, when the follower first contacts the cam surface at approximately 40 degrees flexion, mechanical posterior rollback is initiated due to the differences in articular curvature. In a normal knee, physiological femoro-tibial rollback starts at the onset of knee flexion and is generally mostly completed by 40 degrees of flexion. This rollback is believed to provide substantially a purely rolling motion of the condyles on the tibial plateau bearing surfaces (femoro-tibial motion), after which there is a transitional motion of rolling and sliding. Therefore, it is desirable that the beginning of cam/follower contact for initiation of the posterior rollback phase of knee motion occurs as early as possible in the flexion range, and also that completion of rollback mostly occurs at or preferably before approximately 40 degrees of flexion is experienced. The '547 and '071 patents furthermore describe the action of the cam/follower mechanism of the disclosed devices, in producing posterior rollback, simulating the rolling-type of posterior displacement of the femoro-tibial articular contact in the natural knee during knee flexion. However, the indicated commencement of this roll-back feature in the '547 and '071 patents "begins after flexion of the knee joint through approximately 40 degrees (flexion), and ends after flexion of the joint through approximately 90 degrees (flexion)." In the normal knee, through the complex active interaction of the anterior and posterior cruciate ligaments and other surrounding adjacent soft tissue structures, the rollback phase of femoro-tibial articulation commences early in the flexion range, as aforementioned, and is essentially mostly completed at 40 degrees flexion; with the character of the primary articulation, after completion of posterior rollback, gradually changing to a gliding and then sliding mode in a manner approaching that of a fixed fulcrum posterior condyle rotation.

Third, the geometry or shape of the articular surface of the cam and follower members in the '547 and '071 patents are not described as being congruent, and therefore, the functional contact area is small and the resultant contact stresses are high when joint loading which tends to produce anterior dislocation of the femur in imposed. Articular surface congruence of the cam and follower member is incorporated in the posterior stabilized device described in U.S. Pat. No. 4,888,021. This latter patent utilizes the aforementioned box-like "stabilizer" structure and therefore, requires a large resection of intercondylar femur bone to accommodate accurate seating of the femoral component. The relative advantages of large bearing contact surface, associated with joint prosthesis bearing surface congruency is well known and has been adopted in a number of prosthetic devices for the knee joint, as well as for the other joints of the human body, e.g. the shoulder and hip.

Fourth, the referenced cam and follower members, although of limited height to prevent intrusion within the intercondylar bone space of the distal femur, still occupy an intercondylar position of the reconstructed knee joint which, like the other posterior stabilizing knee prostheses previously referenced and described, generally are principally prescribed in surgical situations where the cruciate ligaments are absent, non-viable and/or are intentionally sacrificed.

In copending application Ser. No. 07/673,790 filed Mar. 22, 1991 by the present inventor, a posterior stabilized knee prosthesis construction is disclosed which distinguished the known prior art in many respects, among them by the provision for cam follower posterior stabilization inboard of the condyles and attempts by such construction to simulate normal knee movement and femoral/tibial interaction. Specifically, the condyles of the respective components rotate and the tendency for the femoral component to move anteriorly during full flexion is prevented by the cam/follower and support.

This construction, however, possesses a drawback, as the cam support and posterior stabilization is disposed inboard of the condyles and thereby cuts off the ability to retain any of the original ligamenture in the instance where surgical removal of less radical nature is possible. A need therefore exists for a posterior stabilized knee construction that can accommodate the retention of certain of the original joint structures while providing the stability, support and longevity of the natural knee.

With regard to hinged knee prostheses, mechanically linked or hinged type of knee prostheses generally provide a fixed fulcrum or uni-axis flexion-extension capability. Some of these devices are fully constrained in axial rotation, while others provide either partially constrained or unconstrained axial rotational freedom. Hinged knee prostheses are surgically indicated in selective cases involving gross and unreconcilable knee joint instability; resulting from major destruction and incompetency of the surrounding soft tissue structures due to previous surgical failure, trauma, disease and congenital related conditions. Mechanical linking of the femoral and tibial prosthetic components by means of a hinge pin connection or some other bearing/connection means functionally compensates for loss of biomechanical knee constrainment and stability; which, is normally provided by the soft-tissue structures surrounding the knee joint.

Examples of uni-axis hinged type knee prosthetic devices are disclosed in U.S. Pat. No. 3,996,624 to Noiles and U.S. Pat. No. 4,136,405 to Pastrick et al. The Noiles and Pastrick et al inventions additionally provide partially constrained femoro-tibial axial rotation (rotating platform concept) with minimal medial-lateral or varus-valgus rotation. Further, the prosthesis disclosed in U.S. Pat. No. 3,837,009 to Walker provides variable axis flexion/extension motion but within the vertical or coronal plane of the knee joint and in a manner which does not involve natural-like posterior femoro-tibial rollback. A vertically oriented tear-drop shape slotted hole in the upwardly extending tibial post provides only vertical displacement of the femoro-tibial instant center, as a function of the multi-radius shape of the femoral condyles. Distal divergence of the vertical slotted hole provides radial clearance for the transverse hinge pin to allow slight axial rotational freedom and slight anterior-posterior freedom, over the latter stages of knee flexion. No provisions are incorporated in the Walker design to produce natural-like femoro-tibial posterior rollback nor posterior and anterior stabilization of knee joint motion.

It is therefore apparent that even hinged constructions suffer from the inability to simulate natural motion of the tibia and femur with respect to each other throughout the full range of knee motion encountered in everyday activity, and that a need therefore exists for a hinged construction that remedies the aforenoted deficiencies.

OBJECTS AND SUMMARY OF THE INVENTION

In view of the above, the present invention provides knee prostheses of significant versatility, that are capable of a broad range of functional capabilities. All of the prostheses presented herein are able to serve as resurfacing type prostheses according to the first category of total knee protheses, where the posterior (and anterior) cruciate ligaments are viable and retained. Additionally, the inventive prostheses are able to function as posterior stabilized total knee prosthetic devices according to the third category, where, the posterior cruciate structures are absent, incompetent or intentionally sacrificed—providing in all instances posterior stabilization from the onset of femoro-tibial flexion and continuing throughout the full flexion range. The present invention offers prostheses meeting the criteria of the second category that include a mechanical hinged connection between the femoral and tibial components.

A central aspect of all of the prosthetic devices of the present invention is the location of the cam and follower means that participate in providing posterior stability, on the outboard lateral aspects of the respective femoral and tibial components. In the first described embodiment, the central area medial to the femoral condyles and the tibial plateau bearing surfaces, respectively, as described herein, is empty, so that any retained natural joint structures such as ligamenture may pass unobstructed therethrough. Accordingly, such device can be used in surgical situations where the long term status of the posterior cruciate ligament structures cannot be reliably ascertained, preoperatively or interoperatively, because of possible continuation of the disease process, overstressing of the ligament structures by improper component design or malalignment, inadvertent or accidental surgical damage, or the like. In the event that the viability of the posterior cruciate ligament structures deteriorates postoperatively due to uncertain pathological, physiological or design related etiology, this first construction of the present invention will continue to provide uninterrupted knee joint function and posterior stabilization without surgical intervention, as its design specifically accommodates both the presence and the absence of the posterior (and anterior) cruciate structures.

Also, the selected geometry and outboard position of the cam and follower members of all of the present prostheses can produce a more natural-like posterior rollback displacement of the femoro-tibial articulation, commencing from the onset of flexion, including the accommodation of maximum hyperextension, and proceeding in a uniform manner to approximately 30 degrees flexion, where rollback is essentially completed.

Upon completion of the rollback phase, the cam member function is uniquely transferred to the outboard portion of the medial and lateral posterior femoral condyles, and the follower member function is transferred to the outboard portion of the respective concave arcuate posterior tibial plateau bearing surfaces—and then traversing back (flip-flop) onto respective surfaces of the concave arcuate follower member, as the flexion angle increases from approximately 30 degrees flexion to full flexion. After completion of posterior rollback, therefore, until the attainment of full flexion, the posterior femoral condyles and mating posterior tibial plateau bearing surfaces provide a concurrent dual functionality: namely, (1) to provide primary femoro-tibial knee joint articulation; and (2) to provide posterior (tibia-to-femur) stabilization. In this manner posterior stabilization continues to occur throughout the entire flexion range; thus, reducing the possibility of anterior dislocation of the femur. Likewise during this flexion phase, the ensuing congruent contact of the posterior femoral condyles with the tibial plateau bearing surfaces and follower member surfaces also provides anterior stability; thus, reducing the possibility of posterior dislocation of the femur.

Furthermore, the aforementioned ensuing flip-flop (second phase) cam/follower function, between the outboard portion of the medial and lateral posterior femoral condyles and respective posterior portions of the concave arcuate tibial plateau bearing surfaces and concave arcuate follower member surfaces, as discussed in detail later on, results in a net increase in articular bearing contact area, which is additive to the femoro-tibial articular bearing contact area, increasing proportionally with the flexion angle from approximately 30 degrees flexion to approximately 55 degrees flexion; where, maximum articular bearing contact area is achieved. From 55 degrees to full flexion, the resulting net effective femoro-tibial bearing surface area is maintained at the maximum level tending to functionally augment the transfer, maintenance and distribution of the higher levels of knee joint loading associated with increased flexion. This is totally unlike conventional resurfacing total knee prostheses (first category) and posterior stabilized total knee prostheses (third category), which generally incorporate non-congruent or "line" contact articular bearing contact pattern geometries in both the femoro-tibial joint and cam/follower mechanism.

The stabilizer cam and follower members that serve as the primary articular bearing surfaces of the present invention are of low profile design and are effectively integrated—not within the conventional intercondylar space—but within the outboard anterior-central sector of the medial and lateral distal femoral condyles. In this manner the need for a "stabilizer box", together with all of its associated potential clinical and functional shortcomings, is avoided. With the integration of the cam/follower mechanism within the dimensional thickness boundary of the distal femoral condyles, the intercondylar space is unobstructed and therefore, does not require intercondylar bone resection to accommodate the femoral component. Furthermore, the intercondylar space is especially free to accommodate the implantation of the knee prosthesis components of the present invention within a compromised knee joint in the presence of retained viable, retained questionably viable, absent, resected incompetent or resected viable posterior (and anterior) cruciated ligament structures.

In accordance with a further embodiment of the invention, a hinged prosthesis is provided that draws upon the structural advantages of the outboard cam/follower construction hereof, in combination with an innovative hinge connection between the femur and tibia. The hinge means includes a second cam and follower means within the intercondylar space that functions as an ancillary load bearing articular structure that assumes some of the impact and loading that the knee joint experiences in motion, and thereby lessens the forces and associated wear that are imposed on the articulating surfaces with the condyles.

Accordingly, it is a principal object of the present invention to provide a total knee prosthesis that has dual clinical applicability, either as a resurfacing total knee prosthesis with functional augmentation of retained posterior (and anterior) cruciate ligament structures, or as a posterior stabilized knee prosthesis with functional compensation for lost or surgically removed posterior (and anterior) cruciate ligament structures.

It is another object of the present invention to provide a total knee prosthesis as aforesaid that offers posterior stabilization of the knee joint—with or without posterior (and anterior) cruciate ligament structures—from the onset of knee flexion and throughout the complete range of flexion.

It is another object of the present invention to provide a total knee prosthesis as aforesaid in which the articulating cam/follower members produce a posterior displacement or rollback function of the femoro-tibial joint in a similar manner as the natural knee.

It is still another object of the present invention to provide a total knee prosthesis as aforesaid that provides congruent contact of the medial and lateral posterior femoral condyles with the respective posterior tibial plateau bearing surfaces and follower member surfaces, and that continues after posterior rollback is completed.

It is a still further object of the present invention to provide a total knee prosthesis as aforesaid that requires no additional femoral and tibial bone resectioning compared to a conventional condylar-type resurfacing or non-posterior stabilizing type of total knee prosthesis of similar component size.

It is yet a further object of the present invention to provide a total knee prosthesis as aforesaid that closely mimics the natural biomechanics of the knee joint as it relates to posterior rollback of the femoro-tibial joint during flexion of the knee.

It is still another object of the present invention to provide a total knee prosthesis as aforesaid in which the follower surface member means are always in contact with the respective cam member surface means, providing posterior stabilization throughout the entire flexion range of the prosthetic knee joint.

It is yet another object of the present invention to provide a total knee prosthesis as aforesaid that defines a hinge connection therein to accommodate total absence of supporting ligamenture.

It is another object of the present invention to provide a total hinged knee prosthesis as aforesaid wherein a hinge is provided that offers improved simulation of natural motion even in hyperextension.

It is another object of the present invention to provide a total hinged knee prosthesis as aforesaid wherein the hinge also defines cam and follower means to accept and distribute the forces imposed on the prosthesis during motion.

It is yet another object of the present invention to provide a total knee prosthesis as aforesaid in which the femoro-tibial joint articular surfaces and the cam-follower member articular surfaces, because of the relatively large contact surface areas therein, can be fabricated from an appropriately compatible ceramic-ceramic, e.g. high density alumina; metal-metal, e.g. cobalt-chrome alloy; or ceramic-metal articular bearing couple.

It is therefore an object of this invention to provide a total knee prosthesis device as aforesaid offering the above features and associated, potential clinical advantages.

These and other objects are achieved in a knee joint prosthetic device, which is comprised of a femoral component, a tibial component and patellar component, suitably designed to restore knee joint function when surgically implanted in the conventional manner to the prepared ends of the femur and tibia, respectively.

The femoral component incorporates a pair of medial and lateral condylar runners, which like the natural counterparts are spatially separated and are of multi-radius geometry. Furthermore, the medial and lateral anterior femoral condyles are integrally interconnected by a flange portion (patellar flange), which provides an articular bearing surface for the resurfaced femoro-patellar joint. The femoral component is comprised essentially of two distinct articular bearing portions: (1) the femoro-tibial joint portion consisting of the medial and lateral anterior condyles, the inboard portion of the medial and lateral distal condyles and the inboard portion of the medial and lateral posterior condyles; and (2) the cam member portion, which is integrated within each distal femoral condyle, consisting of an anterior concave surface portion and a posterior convex cam surface portion. Additionally, after approximately 30 degrees flexion to full flexion, the outboard portion of the medial and lateral posterior femoral condyles assumes a dual functional role; namely as a cam member to provide posterior (and anterior) stabilization and also as an articular member of the femoro-tibial joint to provide primary flexion-extension and secondary rotational and translational motions. The continuous surface geometry and coincident center and radius of curvature of the inboard and outboard portions of the posterior femoral condyles allows biomechanical sharing of articular bearing contact area between the cam/follower mechanism and femoro-tibial joint and hence, sharing of the transfer, sustainment and distribution of imposed joint forces acting across the reconstructed knee joint.

The total prostheses of the present invention are able to simulate natural knee motion and provide increased service due to several characteristics of the construction. For example, after rollback is completed at approximately 30 degrees flexion, the cam member function is transferred from the convex cam member surface integrated within the central-posterior portion of the medial and lateral distal femoral condyles to the outboard portion of the medial and lateral posterior femoral condyles, and the follower member function is transferred from the medial and lateral outboard concave arcuate follower member surfaces to the outboard medial and lateral posterior portion of the concave arcuate tibial plateau bearing surfaces. As the flexion angle increases, the articular path of the outboard-anterior portion of the medial and lateral posterior condyles traverses anteriorly, commencing congruent articulation with the concave arcuate surface of the medial and lateral follower members.

Further, after rollback is completed at approximately 30 degrees flexion, the outboard-anterior portion of the medial and lateral posterior femoral condyles articulates with the outboard portion of the respective concave arcuate posterior tibial plateau bearing surfaces—with the congruent articular path traversing anteriorly, retracing back onto to the respective medial and lateral concave arcuate follower member surfaces, as flexion angle increases to full flexion. This action provides (1) supplementary femoro-tibial joint articular support, and (2) posterior and anterior stabilization of the knee joint. This flip-flop articular path also results in an increase in articular bearing surface area of the cam/follower members, which is additive to the articular bearing surface area of the femoro-tibial joint, increasing proportionally with flexion angle to approximately 55 degrees, where maximum articular bearing surface area is attained. The maximum surface area is maintained throughout the remainder of the flexion range to full flexion, to functionally augment the transfer, maintenance and distribution of the higher levels of femoro-tibial joint loading associated with higher levels of knee flexion.

As used herein, the terms "inboard" and "outboard" are intended to describe the location of the cam member and follower means in relation to the condyles of the femoral component and the plateau regions of the tibial component. Particularly, "inboard" represents a position that is medially and laterally adjacent to the intercondylar space of the femoral component and the central eminence of the tibial component, while "outboard" refers to the locations at the extreme medial and lateral positions of the knee joint.

An intercondylar space or opening within the condyles is formed by the posterior edge of the distal portion of the patella flange at the junction of the anterior and distal condyles, and the medial and lateral edges of the respective lateral and medial femoral condyles. Unlike most conventional posterior stabilized total knee prostheses, the intercondylar opening portion of the present knee prosthesis invention within the region, thickness and plane of the respective condylar boundaries is spatially unobstructed—like conventional posterior cruciate retaining or anterior and posterior cruciate retaining condylar resurfacing types of knee prosthesis designs (of the first category). Hence, the knee design according to the present invention can be surgically employed in clinical situations embracing both sets of surgical indications currently established and accepted for both condylar resurfacing and posterior stabilized types of total knee prostheses.

The interconnecting eminence extends into the intercondylar opening, anteriorly and centrally, but not above the thickness of the distal or posterior femoral condyles of the femoral component. Since its maximum height is not greater than the thickness of the distal or posterior femoral condyles, resection of additional distal femur bone to provide adequate clearance for the height of the eminence is, therefore, not required. The resulting unobstructed spacial design of the region in and about the intercondylar space of the femoral component and the incorporation of an appropriate conventional cruciate "cut-out" located posterior of the interconnecting eminence and between the inboard medial and lateral tibial plateau bearing surfaces, will provide the required clearance for surgically retained posterior (and anterior: deeper cut-out required) cruciate ligament structures; which, constitutes a surgical alternative—not provided by the more conventional types of posterior stabilized total knee prostheses (third category).

The articular surface geometry of the medial and lateral centrally positioned concave arcuate follower member portion has an identical position, profile shape and radius and center of curvature as the inboard and outboard posterior portions of the respective tibial plateau bearing surface members. In the preferred embodiment, the medial and lateral convex cam member contacts the respective centrally positioned concave arcuate follower member surface at the onset of flexion and remains in non-congruent articular contact as the flexion angle increases to approximately 30 degrees flexion. From approximately 30 degrees flexion to full flexion both posterior (and anterior) stabilization and femoro-tibial articulation is provided by the dual functional role assumed by the posterior femoral condyles, coming into congruent contact with the inboard and outboard posterior portions of the tibial plateau bearing surfaces and also with the centrally positioned concave arcuate follower member surfaces. Thus, posterior stabilization occurs over the entire flexion-extension range of the reconstructed knee joint.

At the outset of flexion, the ensuing contact of the medial and lateral convex cam members with the respective centrally positioned concave arcuate follower surface members produces a camming action which displaces the center of curvature of the posterior femoral condyles, posteriorly and toward the center of curvature of the anterior concave arcuate follower members and the inboard and outboard concave arcuate posterior portion of the tibial plateau bearing surfaces; thus, producing a natural-like posterior rollback displacement of the condyles of the femoral component relative to the plateau bearing surfaces of the tibial component. At approximately 30 degrees flexion, the center of curvature of the posterior femoral condyles meets and coincides with the center of curvatures of the concave arcuate follower members and posterior portion of the tibial plateau bearing surfaces to complete posterior rollback of the femoro-tibial joint; hence, the inboard femoro-tibial condylar bearing surfaces and the cam/follower member articular bearing surfaces coincidentally assume a condition of congruent contact after rollback is completed. From this point in the flexion range, (30 degrees flexion) to full flexion, both articular elements will maintain contact congruency. As will be discussed in more detail later on, the net articular bearing contact area of the femoro-tibial joint attains a maximum value at approximately 30 degrees flexion and maintains this level of articular contact area at a constant value over the remainder of the flexion range. The congruent articular bearing contact area of the cam/follower members increases proportionally with flexion angle from approximately 30 degrees flexion and reaching a maximum value at approximately 55 degrees flexion. From this point in the flexion range to full flexion, the net articular surface area of the cam and follower members—which is additive to the femoro-tibial articular bearing contact surface area—remains constant at the maximum value.

Additionally, as another principal embodiment of the present invention, from the point in the flexion range where femoro-tibial rollback is completed at approximately 30 degrees flexion to full flexion, the outboard portion of the medial and lateral posterior condyles mechanically "link-up" or commence articulation with the articular surface of the respective follower members; thus functioning thereon as the medial and lateral cam members. The inboard portion of the medial and lateral posterior condyles remain in congruent contact with the inboard posterior portion of the medial and lateral tibial plateau bearing surfaces within this flexion range (30 degrees to full flexion) in the usual manner to provide primary flexion-extension femoro-tibial articulation.

As still another embodiment of the present invention, the resulting medial and lateral posterior condyle/follower member articular contact, as described, provides posterior and anterior knee joint stabilization within this flexion range and also, uniquely provides additional femoro-tibial articular bearing surface area, which proportionally increases in magnitude as flexion angle increases, up to approximately 55 degrees flexion. Further, as the radius of curvature of the medial and lateral posterior condyles is identical to the radius of curvature of the medial and lateral concave arcuate follower members and inboard and outboard posterior portions of the medial and lateral tibial plateau bearing surfaces, the resulting posterior condyle/follower member congruent articular bearing contact area compliments, augments and works in conjunction with the congruent femoro-tibial condylar articular bearing contact area from about 30 degrees flexion, to full flexion—increasing proportionally with flexion angle up to about 55 degrees and remaining at this level, thereafter to full flexion. In this way, a large net effective femoro-tibial joint articular bearing contact area is provided, that for the present invention with intermediate sized knee prosthesis components is equivalent to a 32 mm femoral (hip) head. Large articular contact area is known to reduce contact stresses and associated plateau (and follower member) bearing surface wear and damage, and the potential accompaniment of improved in-situ knee implant (UHMWPE) bearing service life.

Required bone resection at the anterior, distal and posterior aspects of the distal femur to allow accurate seating of the femoral and tibial components of the present invention is essentially consistent to the resection requirements of most conventional condylar resurfacing types of knee prostheses. This feature is provided, since the height of the medial and lateral cam and follower members of the stabilizer mechanism is designed to be within the maximum thickness of the distal and posterior condyles of the femoral component. The resulting potential clinical advantage relates to enhanced surgical versatility, associated with selecting for implantation a knee prosthesis which embraces the surgical indications of either a condylar resurfacing type or posterior stabilized type of total knee prosthesis with minimal femoral and tibial bone resection, e.g. without requiring the resection of a substantial block of intracondylar distal femur bone to accommodate a conventional "stabilizer box". Additionally, minimal femoral and tibial bone resection, during knee joint reconstruction, is universally recognized as a desirable surgical alternative for a number of obvious clinical reasons—one of which relates to the presence of stronger and denser bone stock at levels closest to the condylar surface, and the other of which relates to greater retained bone mass and associated potentially easier surgical course in the event implant revision is required at a later date.

In a further aspect, the UHMWPE tibial bearing component of the present invention is designed to provide both condylar resurfacing and posterior stabilization. In conventional knee prosthesis systems the UHMWPE tibial plateau bearing component for a resurfacing condylar type of knee prosthesis is unique or different than one which is designed for posterior stabilization. The femoral component exhibits a similar interchangeability limitation. The dual functionality of the present invention could result in less overall system complexity and reduced implant inventory requirements. Surgical instrumentation can also be significantly simplified; since, the various (and numerous) alignment fixtures, resection guides, provisional trial components, etc., can readily accommodate both condylar resurfacing and posterior stabilized types of knee joint reconstructions.

In accordance with a first aspect of the present invention, a knee prosthesis capable of providing resurfacing to the adjacent ends of the existing bone structures, as well as total posterior stabilization to the knee joint, is provided that comprises:

a) a femoral component including:
  i) a medial condyle having an anterior portion, a distal portion and a posterior portion;
  ii) a lateral condyle having an anterior portion, a distal portion and a posterior portion;
  iii) an anterior patella flange interconnecting the anterior portions of the medial and lateral condyles in parallel, spaced apart relation; and
  iv) cam member means integral with said medial and lateral condyles and located outboard thereof, said cam member means having an anteriorly located concave cam member surface and a posteriorly located convex cam member surface;

b) a tibial component including:
  i) multi-radius tibial plateau bearing surface means for receiving said medial and lateral condyles for rolling and sliding movement thereon; and
  ii) follower member means integral with said bearing surfaces for receiving the cam surfaces of said cam member means for rotational and sliding movement thereon; and c) the cam member surfaces of said cam member means being in contact with said follower member means for substantially the entire flexion range of the reconstructed knee joint.

In accordance with another aspect of the present invention, a total knee prosthesis is provided that comprises:

a) a femoral component including:
  i) a medial condyle having an anterior portion, a distal portion and a posterior portion;
  ii) a lateral condyle having an anterior portion, a distal portion and a posterior portion;
  iii) an anterior patella flange interconnecting the anterior portions of the medial and lateral condyles in parallel, spaced apart relation; and
  iv) cam member means integral with said medial and lateral condyles and located outboard thereof, said cam member means having an anteriorly located concave cam member surface and a posteriorly located convex cam member surface;

b) a tibial component including:
  i) multi-radius tibial plateau bearing surface means for receiving said medial and lateral condyles for rolling and sliding movement thereon; and
  ii) follower member means integral with said bearing surfaces for receiving the cam surfaces of said cam member means for rotational and sliding movement thereon; and c) said convex cam member surface being in sliding contact with said follower member means to provide posterior rollback of said condyles on said tibial plateau bearing surface means during flexion, starting at starting at the outset of flexion (approximately maximum normal hyperextension of flexion), and being completed at an angle less than approximately 40 degrees (approximately 30 degrees) of flexion.

In a still further aspect of the present invention, a knee prosthesis capable of providing resurfacing to the adjacent ends of the existing bone structures, as well as total posterior stabilization to the knee joint, is disclosed which comprises:

a) a femoral component including:
  i) a medial condyle having an anterior portion, a distal portion and a posterior portion;
  ii) a lateral condyle having an anterior portion, a distal portion and a posterior portion;
  iii) an anterior patella flange interconnecting the anterior portions of the medial and lateral condyles in parallel, spaced apart relation; and
  iv) a cam member means integral with said medial and lateral condyles and located outboard thereof, said cam member means having an anteriorly located concave cam member surface and a posteriorly located convex cam member surface;

b) a tibial component including:
  i) multi-radius tibial plateau bearing surface means for receiving said medial and lateral condyles for rolling and sliding movement thereon; and
  ii) follower member means integral with said bearing surfaces for receiving the cam surfaces of said cam member means for rotational and sliding movement thereon; and c) the outboard portion of the medial and lateral posterior femoral condyles being in congruent contact with the outboard posterior portion of the tibial plateau bearing surface means at the completion of posterior rollback at approximately 30 degrees flexion and then retracing back anteriorly to the centrally positioned concave arcuate follower member means, as flexion angle increases from approximately 30 degrees flexion to full flexion.

In a still further aspect of the invention, a total knee prosthesis capable of providing resurfacing to the adjacent ends of the existing bone structures, as well as total posterior stabilization to the knee joint, is disclosed that comprises:

a) a femoral component including:
  i) a medial condyle having an anterior portion, a distal portion and a posterior portion;
  ii) a lateral condyle having an anterior portion, a distal portion and a posterior portion;
  iii) an anterior patella flange interconnecting the anterior portions of the medial and lateral condyles in parallel, spaced apart relation; and
  iv) cam member means integral with said medial and lateral condyles and located outboard thereof, said cam member means having an anteriorly located concave cam member surface and a posteriorly located convex cam member surface;

b) a tibial component including:
  i) multi-radius tibial plateau bearing surface means for receiving said medial and lateral condyles for rolling and sliding movement thereon; and
  ii) follower member means integral with said bearing surfaces for receiving the cam surfaces of said cam member means for rotational and sliding movement thereon; and c) hinge means associated with and hingeably connecting said femoral component and said tibial component;

d) the cam member surfaces of said cam member means being in contact with said follower member means for substantially the entire flexion range of the knee.

Still further, the present invention extends to a hinge assembly for use in a knee prosthesis adapted to provide hingeable connection between a femoral component and a tibial component of such knee prosthesis, and to offer posterior stabilization thereto, said hinge assembly comprising:

a) plural spaced apart femoral hinge components;
b) a tibial hinge component located between said femoral hinge components;
c) a hinge axis comprising a hinge pin extending between said femoral hinge components and said tibial hinge components;
d) hinge-related posterior stabilization means comprising cam means defined by said tibial hinge component and follower means defined by said femoral hinge components.

The above and other objects, features and advantages of the present invention will become apparent from the following detailed description of the invention, when considered in conjunction with the accompanying drawings.

BRIEF DESCRIPTION OF THE DRAWINGS

FIG. 1 is a front elevational view of a prosthesis according to an first embodiment of the present invention, partly exploded for clarity.

FIG. 2 is a medial side elevational view of the knee prosthesis of FIG. 1, shown with all components in reduced or assembled mode, with the anterior aspect being to the left and the posterior aspect being to the right of the drawing;

FIG. 3 is a rear (posterior) view of the prosthesis of FIG. 1, shown with all components in reduced or assembled mode, with the right side of the drawing being lateral;

FIG. 4 is a front (anterior) view of the femoral component of knee prosthesis of FIG. 1, showing the positional relationship of the patella flange, the anterior aspects of the medial and lateral condyles, the inboard distal femoral condyles and the outboard cam member means integrated within the medial and lateral distal femoral condyles, with the left side of the drawing being lateral;

FIG. 5 is a medial side elevational view of the femoral component of FIG. 4, showing the medial cam member means integrally incorporated within the dimensional thickness of the medial distal femoral condyle, consisting of a concave surface anteriorly and the convex cam member posteriorly, with the anterior aspect being to the left of the drawing;

FIG. 6 is a top plan view of the femoral component of FIG. 4, showing the obvious absence of a conventional intercondylar "stabilizer box" and the spatially unobstructed design of the intercondylar space, with the anterior aspect being to the lower side of the drawing and the lateral aspect being to the left of the drawing;

FIG. 7 is a bottom plan view of the femoral component of FIG. 4, showing the positional relationship of the inboard femoral distal condyles and the cam member means integrally incorporated within the outboard portion of the medial and lateral distal femoral condyles, with the anterior aspect being to the top and the lateral aspect being to the left of the drawing;

FIGS. 8a–8c are medial side (exploded) elevational views of the tibial component of the knee prosthesis of FIG. 1, showing the mode of assembly, dovetail channel assembly constrainment and screw securement of the UHMWPE tibial plateau bearing component with the mating tibial base component, with the anterior aspect being to the left and medial aspect being the forward or frontal view of the drawing; FIG. 8b is a side elevational view of the medial side view of the UHMWPE tibial plateau bearing component showing the multi-radius articular geometry of the inboard femoro-tibial surface means and the outboard follower member means consisting of the anterior convex surface member and the centrally positioned concave arcuate follower surface member with connecting inboard (and outboard) posterior portion of the tibial plateau bearing surface means.

FIG. 9 is a top plan view of the UHMWPE tibial plateau bearing component shown in FIG. 8b, showing the positional relationship of the inboard femoro-tibial condylar bearing surfaces, interconnecting central eminence with screw port, the outboard follower member means and the posteriorly situated posterior cruciate clearance cut-out (an anterior cruciate cut-out would be deeper, anteriorly), with the left side of the drawing being anterior and the upper side of the drawing being lateral;

FIG. 10 is a bottom plan view of the UHMWPE tibial plateau bearing component shown in FIG. 8b, showing the layout of the peripheral and central constraining dovetail channels and anterior location of the screw thread clearance port, with the left side of the drawing teeing anterior and the lower side of the drawing being lateral;

FIG. 11 is a top plan view of the tibial base component as shown in FIG. 8a, showing the posterior cruciate ligament clearance cut-out and relative positions of the peripheral and central constraining dovetail channels, with the left side of the drawing being anterior and the upper side being lateral;

FIG. 12 is a bottom plan view of the tibial base component shown in FIG. 8a, showing the porous coating means, intramedullary stem with stabilizing gussets and stabilizing fixation pegs, with the left side of the drawing being anterior and the lower side being lateral;

FIG. 13 is a medial side elevational view of the knee prosthesis shown in FIG. 1—except the femoral component and tibial plateau bearing component are depicted in reduced relative position at the outset of flexion at 6 degrees of hyper-extension, with the left side of the drawing being anterior and the right side being posterior;

FIGS. 14a–14e are medial side elevational views of the knee prosthesis shown in FIG. 1, where the femoral component and tibial plateau bearing component are depicted in several reduced relative functional positions corresponding to the outset of flexion at 0 degrees flexion, an intermediate position at 15 degrees flexion prior to completion of posterior femoro-tibial rollback, completion of posterior rollback at approximately 30 degrees flexion, attainment of maximum cam/follower articular bearing contact area at approximately 55 degrees flexion, and at 120 degrees maximum flexion are shown to demonstrate the biomechanical interaction of the components and the congruent path of articular mechanics of the outboard medial (and lateral) cam/follower mechanism—shown by the solid triangles—and of the inboard medial (and lateral) femoro-tibial joint—shown by the empty triangles.

FIG. 15 is a front (anterior) elevational view of a mechanically linked variable axis total knee prosthesis 110 according to an embodiment of the invention in which the femoral component 112 is depicted reduced with the tibial component 114 being comprised of the tibial plateau bearing component 157 assembled onto the tibial base component 184. It should be noted that a right-side knee prosthesis is shown, in which the left side is the lateral aspect and the front view is the anterior aspect. A total knee prosthesis for left-side knee arthroplasty would incorporate a femoral component, a mirror image of that shown in FIG. 15 in which the right side would be the lateral aspect. The tibial plateau bearing component 157 and the tibial base component 184 are symmetrically designed and hence, universally applicable to both right and left-side femoral components of comparable size;

FIG. 16 is a medial side elevational view of the total knee prosthesis of FIG. 15, shown with all components in reduced or assembled position, with the anterior aspect being to the left and the posterior aspect to the right;

FIG. 17 is a rear (posterior) elevational view of the total knee prosthesis of FIG. 15, shown with all components in reduced or assembled position, with the right side of the drawing being lateral;

FIG. 18 is a front (anterior) elevational exploded view of the total knee prosthesis of FIG. 15, showing femoral component 112 in assembly alignment with the tibial component 114 and hinge pin 115. The left side of the drawings being the lateral aspect and the frontal view being anterior.

FIG. 19 is a front (anterior) elevational view of the femoral component of the total knee prosthesis of FIG. 15, showing the positional relationship of the patella flange 136, the anterior aspects 128 and 130 of the medial and lateral femoral condyles 116 and 118, the medial and lateral inboard distal femoral condyles 124a and 126a and the medial and lateral outboard cam member means 132, with the left side of the drawing being lateral;

FIG. 20 is a medial side elevational view of the femoral component of FIG. 19 showing the medial outboard cam member means 132 being comprised of a concave portion 132b anteriorly and convex cam member portion 132a posteriorly, integrally incorporated within the outboard portion of medial distal femoral condyle 124 with the convex cam member portion 132a in smooth transition with the outboard portion 120b of the medial posterior femoral condyle 120, with the anterior aspect being to the left of the drawing;

FIG. 21 is a top plan view of the femoral component of FIG. 19 showing fixation surfaces: anterior 140, anterior-distal 142a and 142, distal 144 and 146, posterior 152 and 154 and central surfaces 125, 127 and 131 with metallurgically applied porous surface structure means 156; and centrally positioned intercondylar housing 137 with intermedullary stem 139, which interconnects the lateral surface aspect 116a of medial femoral condyle 116 and the medial surface aspect 116b of lateral femoral condyle 118, with the anterior aspect being to the lower side of the drawing and the lateral aspect being to the left;

FIG. 22 is a bottom plan view of the femoral component of FIG. 19 showing the positional relationship of the medial and lateral inboard distal femoral condyles 124a and 126a with the respective anterior condylar aspects 128 and 130, with the inboard portions 120a and 122a and outboard portions 120b and 122b of respective posterior condyles 120 and 122, with the cam member means 132 integrally incorporated within the outboard portion of the medial and lateral distal femoral condyles 124 and 126 and with the interior surface portions 129, 116a and 116b of the centrally positioned interconnecting intercondylar housing 137 with the anterior aspect being to the top of the drawing and the lateral aspect being to the left;

FIGS. 23a–23d are medial side (exploded) elevational views of tibial component 114 of the knee prosthesis of FIG. 15 showing assembly alignment, mode of dovetail channel 183 and 183a engagement and screw 193 securement means of the tibial plateau bearing component 157 with the mating tibial base component 184 and threaded assembled tibial end plug 189; additionally depicted are the multi-radius articular geometry of the inboard femoro-tibial bearing surface means 158, the slotted transverse port 115d with anterior center-axis O and posterior center-axis O' for hinge pin 115 assembly and the outboard follower member means 176 consisting of anterior convex surface portion 178a and central concave arcuate follower surface portion 178, smoothly connected posteriorly to the outboard and inboard portions of the posterior tibial plateau bearing surface means 162a and 162 with the anterior aspect being to the left of the drawing and the medial aspect being the front view.

FIG. 24 is a top plan view of the tibial plateau bearing component 157 shown in FIG. 23c, showing the positional relationship of the inboard tibial plateau bearing surfaces 158 and 160, centrally positioned interconnecting tibial post 174 with screw port 175 and outboard follower member means 176 with the left side of the drawing being anterior and the upper side being lateral, relative to the assembly orientation of the total knee prosthesis of FIG. 15;

FIG. 25 is a bottom plan view of the tibial plateau bearing component 157 in FIG. 23c, showing the layout of the side posterior peripheral and central engaging dovetail channels 183a integral with supporting surface 177 and anterior location of the screw thread clearance port 175 with the left side of the drawing being anterior and the lower side of the drawing being lateral relative to assembly orientation of FIG. 15;

FIG. 26 is a top plan view of the tibial base component 184 in FIG. 23a, showing the relative positions of the side-posterior peripheral and central engaging dovetail channels 183 and anterior-central threaded screw port 187 with the left side of the drawing being anterior and the upper side being lateral relative to assembly orientation of FIG. 15;

FIG. 27 is a bottom plan view of the tibial base component 184 in FIG. 23a, showing the porous coated fixation surface means 188 in partial section, intramedullary stem 191 with stabilizing gussets 192 and stabilizing fixation pegs 190 with the left side of the drawing being anterior and the lower side being lateral relative to assembly orientation of FIG. 15;

FIG. 31 is a medial side elevational view of a uni-axis design version of the total knee prosthesis shown in FIG. 15 with numerical designations of similar portions being advanced by the number 100 and with the left side of the drawing being the anterior aspect and the frontal view being the medial aspect;

FIG. 32 is a rear (posterior) sectional view of the total knee prosthesis shown in FIG. 31, showing the assembled position of hinge pin 215 within the transverse ports 215b and 215a of posterior femoral condyles 220 & 222 and within circular hole 215d in upwardly extending tibial post 274 with the right side of the drawing being the lateral aspect of the uni-axis hinge prosthesis and the background direction being anterior;

FIGS. 33a–33c are lateral sectional views, through the indicated central sectional plane of the total knee prosthesis shown in FIG. 31, where the articular mechanics are depicted at the outset of flexion (FIG. 33a), at an intermediate position of 25 degrees flexion (FIG. 33b) and at maximum flexion of 140 degrees and with the extent of articular bearing contact of the inboard femoro-tibial joint being indicated by empty triangles, the extent of articular bearing contact of the outboard femoro-tibial (previously denoted as the cam/follower) bearing surfaces being indicated by solid triangles and the extent of articular contact of the interior surface 229 of intercondylar housing 237 and contacting bearing surfaces 274a & 274c of upwardly extending tibial post 274 being indicated by solid squares with the left side of the drawings being the anterior aspect and the right side being posterior.

DETAILED DESCRIPTION OF THE PREFERRED EMBODIMENTS

Figures 28A, 28B, 28C:
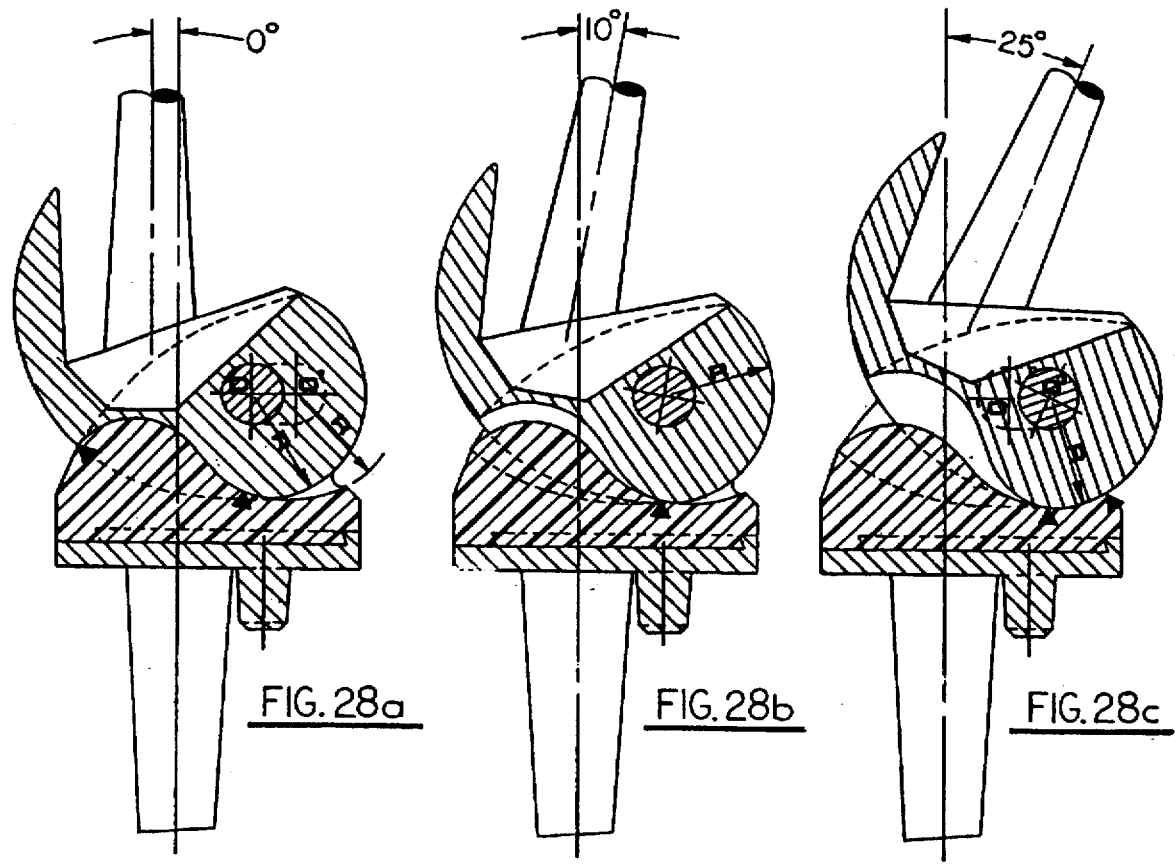
FIGS. 28a–28e are (mirror image) sectional views of the total knee prosthesis shown in FIG. 15 through Section A—A, where the articular mechanics of the lateral (similarly the medial) outboard cam/follower mechanism are depicted at several functional positions corresponding to the outset of flexion at 0 degrees flexion (FIG. 28a), an intermediate position at 10 degrees flexion (FIG. 28b), completion of posterior femoro-tibial rollback at approximately 25–30 degrees flexion (FIG. 28c), attainment of maximum cam/follower bearing contact area at approximately 75 degrees flexion (FIG. 28d) and at 135 degrees maximum flexion (FIG. 28e) and where the extent of cam/follower bearing contact area being indicated by the A–P contact length, as shown by solid triangles with the anterior aspect being to the left and posterior to the right.
Figures 28D, 28E:
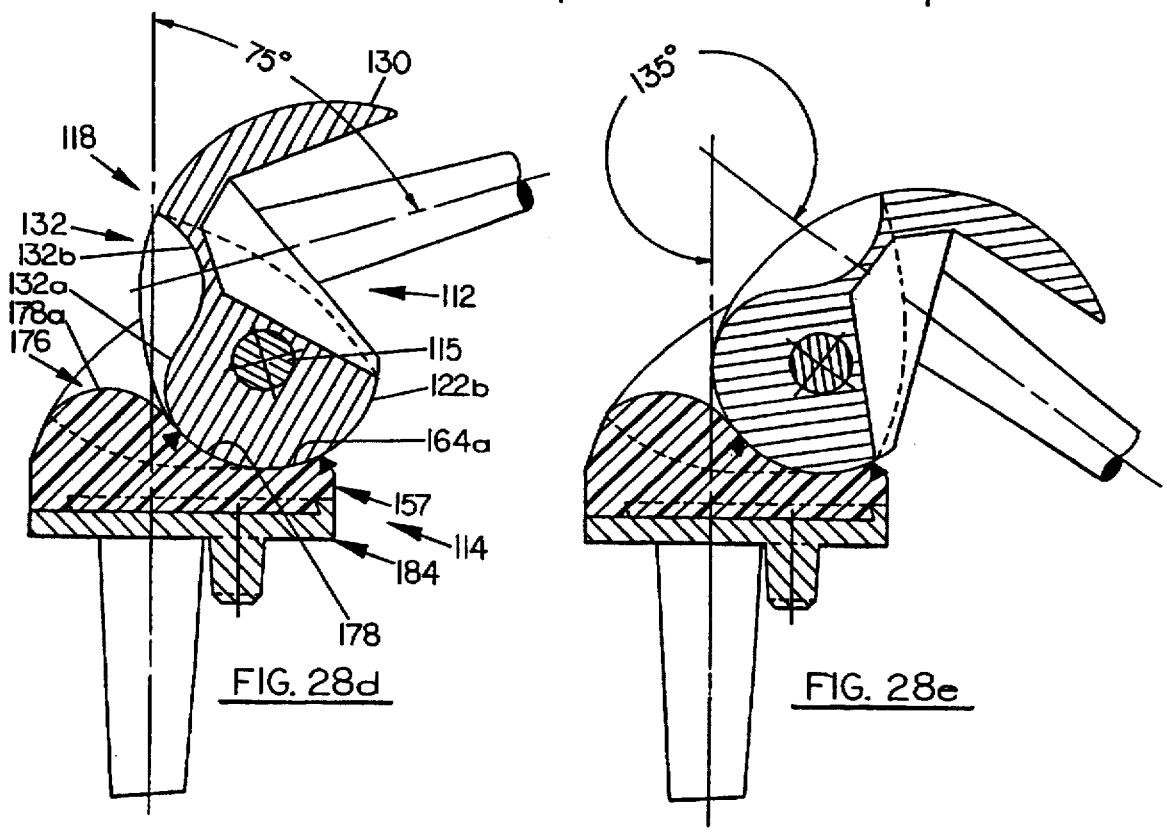

The present invention pertains to a knee prosthesis which (a) can be utilized for primary resurfacing of the articular surfaces of the knee joint, while retaining the posterior (and anterior) cruciate ligament structures—in the same manner as a number of currently available conventional condylar resurfacing types of total knee prostheses and (b) can also be utilized to provide posterior stabilization, e.g. tibia-to-femur constraint, throughout the entire range of flexion and extension; thus, reducing the possibility of anterior subluxation or dislocation of the distal femur in clinical situations involving incompetent, absent or purposely sacrificed posterior cruciate ligament structures or in the presence of inherent posterior tibial instability.

In this regard, therefore, the present prosthesis is categorized as a condylar resurfacing type of total knee prosthesis or a (totally) posterior stabilized total knee prosthesis device. This is accomplished without the need of a conventional "stabilizer box" or other cumbersome mechanical gadgetry, which must be accommodated by substantial resection of viable femur bone stock or which requires the complete sacrifice of the cruciate ligament structures for clearance purposes—even in clinical situations where viable ligament structures may exist at the time of surgery.

Furthermore, in the present invention the posterior stabilizer cam/follower members, are uniquely integrated within the outboard portion of the medial and lateral distal femoral condyles and respective outboard portions of the UHMWPE tibial plateau bearing component and are specially designed to provide both posterior stabilization and a natural-like femoro-tibial posterior rollback, commencing at the outset flexion (at 0 degrees flexion or maximum hyperextension at about −6 degrees flexion) and completing at approximately 30 degrees flexion. From 30 degrees flexion to full-flexion, both the cam/follower member means and the femoro-tibial member means attain a state of congruent contact, which minimizes contact stress. Additionally, upon completion of the posterior rollback phase, the geometry of the contacting articular bearing surfaces provides posterior (and anterior) stabilization of the knee joint; thus, reducing the possibility of anterior (and posterior) subluxation or dislocation of the distal femur.

After the rollback phase, the outboard positioned posterior stabilizer members function in concert with the inboard positioned medial and lateral femoro-tibial condylar bearing members to sustain, transfer and distribute the imposed knee joint reaction forces to the underlying component fixation interfaces and adjacent supportive bone structure. The net effective articular bearing contact area, the summation of that provided by the cam/follower member means and by the femoro-tibial condylar bearing member means, of the present invention is relatively substantial, increasing proportionally with flexion angle and attaining a maximum value at 55 degrees flexion equivalent to a 32 mm femoral (hip) head for intermediate sized knee components. From 55 degrees flexion to maximum flexion the net effective articular bearing contact area is maintained at a constant value equal to the maximum level; therefore, tending to maintain a more acceptable and uniform level of contact stress within the functional range, usually associated with higher levels of joint loading, than most other resurfacing or posterior stabilizing types of total knee prosthesis designs.

Referring now to the Figures wherein like numerals designate like parts and particularly to FIG. 1, knee prosthesis 10 according to a first embodiment of the present invention includes a femoral component 12 and a corresponding tibial component 14. Femoral component 12 incorporates multi-radius medial and lateral condylar runners or condyles 16 and 18, which mimic the natural femoral condyles of the distal femur that they replace. Specifically, medial and lateral femoral condyles 16 and 18 include three distinct portions, that is, respective medial and lateral posterior condyle portions 20 and 22, distal femoral condyle portions 24 and 26, and anterior femoral condyle portions 28 and 30.

It is a particular feature of the invention that the medial and lateral distal femoral condyles 24 and 26 consist of inboard femoro-tibial distal femoral condyles 24a and 26a and outboard medial and lateral cam members 32. The medial and lateral cam members 32 consist of an anterior concave surface portion 32b and posterior convex cam member portion 32a. The medial and lateral posterior femoral condyles 20 and 22 consist of medial and lateral inboard portions 20a and 22a and medial and lateral outboard portions 20b and 22b. The surface geometry of the inboard portions, 20a and 22a, and outboard portions 20b and 22b, of the respective posterior femoral condyles 20 and 22 is continuous and has the same radius of curvature R and center of curvature O (FIG. 5).

In addition, femoral component 12 includes medial and lateral cam members 32, integrally positioned within the outboard portion of the medial and lateral distal femoral condyles 24 and 26, between the anterior femoral condyles 28 and 30 and posterior femoral condyles 20 and 22 of medial and lateral femoral condyles 16 and 18, respectively. As shown in the first embodiment of FIGS. 1–12, cam members 32 are formed in two parts: the anterior concave surface portion 32b and the posterior convex portion 32a, each integral within the outboard portion of medial and lateral distal femoral condyles 24 and 26. Further, the radius of curvature R of the convex cam member 32a is identical to the radius of curvature R of the posterior portions 20 and 22 of the medial and lateral femoral condyles 16 and 18, the radius of curvature R of the outboard (anterior to line 82) concave arcuate follower members 78, the radius of curvature R of the outboard posterior portion of tibial plateau bearing surfaces 62a and 64a and the radius of curvature R of the inboard posterior portion of the medial and lateral tibial plateau bearing surfaces 62 and 64, with the respective centers of curvature located at points O and O', as shown in FIGS. 2, 5 and 14a.

The anterior portion of femoral component 12 is formed of the aforementioned anterior portions 26 and 30 of medial and lateral condyles 16 and 18, and an anterior patellar flange 36 integral with and interconnecting anterior portions 28 and 30. The patella member 94 (shown in phantom) articulates with the anterior patellar flange 36, biased laterally at the outset of flexion, and gradually transfers articulation in a natural-like manner to the distal aspects of the anterior patellar flange 36 and the anterior condyle portions 28 and 30 at approximately 25–30 degrees flexion. From this point on during flexion and as the flexion angle increases to full range, the patellar-femoral joint articulation progresses to the inside corners 38 (FIGS. 4 and 7) of distal femoral condyle portions 24 and 26.

It is noted that the inside surfaces of femoral component 12 which interface directly with bone in the biological fixation mode or with an interpositional thickness of polymethyl methacrylate (PMMA) bone cement in the cemented mode, are the inner anterior surface 40, the inner anterior-distal surface 42, the inner medial and lateral distal surfaces 44 and 46, the inner medial and lateral distal-posterior surfaces 48 and 50, and the inner medial and lateral posterior surfaces 52 and 54. These surfaces may metallurgically incorporate an integral sintered, diffusion bonded or plasma sprayed porous surface structure 56, only a portion of which is shown in FIGS. 4 and 6, as a component biological or cemented fixation means. In addition, upwardly extending cylindrical posts 55 may be provided which fit into appropriately prepared holes in the distal end of the femur to aid in the translational and rotational fixation stability of the implanted femoral component.

In accordance with the invention, the maximum height of the cam members 32, the follower members 76 and the central tibial eminence 74 do not extend beyond the thickness dimension of the distal femoral condyles 24 and 26 and posterior femoral condyles 20 and 22 of medial and lateral femoral condyles 16 and 18, at the level of the inside (bone-side) surface of inner distal surfaces 44 and 46, inner distal-posterior surfaces 48 and 50 and inner posterior surfaces 52 and 54. Additionally, the maximum width of the cam members 32, shown in FIG. 4 as approximately half the overall distal condylar width, does not spatially obstruct the intercondylar space 37, as shown in FIGS. 6 and 7. As a consequence of this design, the stabilizer box structure common to most other posterior stabilizing total knee designs, is not required and accommodation of the femoral component by resecting a significant "block" of viable bone from the intercondylar sector of the distal femur is unnecessary. In addition, as previously stated, the intercondylar space 37 is spatially unobstructed, which can provide sufficient containment clearance for retained cruciate ligament structures, as a surgical alternative—even when current and long term viability status of the structures cannot accurately be preoperatively or interoperatively ascertained.

Further, the intercondylar opening 37 within the condyles 16 and 18 is formed by the posterior edge 29 of the anterior patellar flange 36 and the medial and lateral edges 16a and 16b of the respective medial and lateral condyles 16 and 18. As previously stated, the boundaries of opening 37 are essentially within the plane and maximum thickness of the distal femoral condyles 24 and 26 and posterior femoral condyles 20 and 22 of respective medial and lateral femoral condyles 16 and 18. However, an intercondylar stabilizer box, which generally (a) houses the cam/follower mechanism, (b) positionally invades the intercondylar space, and (c) protrudes within the bone space of the distal femur requiring absolute sacrifice of the posterior (and anterior) cruciate ligaments and substantial removal of distal femoral bone to provide the necessary clearance for component implantation, is not required by the present invention.

The UHMWPE tibial plateau bearing component 57 includes inboard equi-spaced concave multi-radius medial and lateral tibial plateau bearing surfaces 58 and 60, respectively, which receive convex multi-radius medial and lateral femoral condyles 16 and 18, consisting of anterior condylar portions 28 and 30, inboard distal femoral condylar runners 24a and 26a and inboard portions 20a and 22a of posterior femoral condyles 20 and 22, for articulation thereon. In like manner to condyles 16 and 18, and because of the convex multi-radius shape of tibial plateau bearing surfaces 58 and 60, it will be appreciated that tibial plateau bearing surfaces 58 and 60 include anterior portions 70 and 72, central portions 66 and 68, and posterior portions 62 and 64, respectively.

Between medial and lateral tibial plateau bearing surfaces 58 and 60, tibial plateau bearing component 57 includes an interconnecting, centrally positioned and anterior-posterior traversing tibial eminence 74. During the early stages of flexion, the tibial eminence 74 is positioned between the inside corners 38 and side walls 16a and 16b of inboard distal portions 24a and 26a of medial and lateral femoral condyles 16 and 18, respectively, as shown best in FIGS. 1 and 3, providing medial-lateral, axial and varus-valgus rotational knee constraint.

The degree of translational and rotational freedom exhibited by prostheses is a function of the dimensional clearance between the intercondylar space 37 of femoral component 12 between distal portions 24a and 26a of medial and lateral condyles 16 and 18, and the medial lateral width of the tibial plateau bearing eminence 74. As the flexion angle increases, the inboard posterior femoral condyles 20a and 22a of medial and lateral condyles 16 and 18 span the posterior portion of eminence 74. At the outset of flexion or maximum hyperextension, the distal aspect of the anterior condylar portions 28 and 30 and the anterior aspect of the inboard medial and lateral distal femoral condyles 24a and 26a of medial and lateral condyles 16 and 18, congruently contact the anterior portions 70 and 72 of inboard medial and lateral tibial plateau bearing surfaces 58 and 60, respectively; and the concave surface portion 32b of medial and lateral cam member 32 congruently contacts the convex portions 78a of medial and lateral follower members 76, respectively—as best shown in FIG. 2—which provides both posterior (tibia-to-femur) and anterior (femur-to-tibia) stabilization of the hyperextended or 0 degree flexed knee joint.

In addition, tibial plateau bearing component 57 includes outboard medial and lateral follower member means 76 consisting of respective anterior convex surface 78a, central concave arcuate follower member surfaces 78, which extend anterior of mid-line 82 and outboard posterior portion of the concave arcuate tibial plateau bearing surfaces 62a and 64a, which extend posterior of mid-line 82. The medial and lateral cam members 32 of femoral component 12 include a anterior concave surface portion 32b and a posterior convex portion 32a; after posterior rollback is completed at approximately 30 degrees flexion the cam member function is transferred to the outboard portion 20b and 22b of the medial and lateral posterior femoral condyles 20 and 22, respectively.

It will be appreciated that the concave arcuate follower members 78, the outboard posterior portion of the tibial plateau bearing surfaces 62a and 64a and inboard posterior portion of the tibial plateau bearing surfaces 62 and 64 are defined by the identical radius of curvature R, with the common center of curvature located at point O'. Similarly, the convex cam member portion 32a of medial and lateral cam members 32 is also defined by radius of curvature R centered at O', and the radius of curvature of the inboard portion, 20a and 22a, and the outboard portion, 20b and 22b of the medial and lateral posterior femoral condyles 20 and 22 is also equal to R; with the center of curvature located at point O—as is best shown in FIGS. 2 and 5.

At the outset of knee flexion—corresponding to 6 degrees hyperextension (FIG. 13) or at 0 degrees flexion (FIG. 14a), depending upon selected design criteria—the anterior concave cam member surface 32b and anterior convex follower surface 78a come into congruent contact and the anterior face of the convex cam members 32a of medial and lateral cam members 32 congruently contacts the concave arcuate follower member 78, slightly anterior of the mid-line 82. This contact state between the respective cam members 32b and 32a and follower members 78a and 76 represents the earliest stage of posterior (tibia-to-femur) stabilization, which occurs at the earliest stage of knee flexion.

As the flexion angle increases (FIG. 14b), the camming action between the non-congruent contact of the anterior face of convex cam member portions 32a of medial and lateral cam members 32 and the upward sloping concave arcuate follower member portions 78 of medial and lateral follower members 76, respectively, causes the center of curvature O of the medial and lateral posterior condyles 20 and 22 of femoral component 12 to displace posteriorly and approach the center of curvature O' of the concave arcuate follower member portions 78, the outboard posterior portion of the tibial plateau bearing surfaces 62a and 64a, and the inboard posterior portion of the tibial plateau bearing surfaces 62 and 64. This allows the medial and lateral femoral condyles 16 and 18 of femoral component 12 to translate or roll back, posteriorly, relative to the inboard medial and lateral tibial plateau bearing surfaces 58 and 60 of tibial bearing component 57.

Posterior rollback of the femoro-tibial joint continues as the flexion angle increases and at 30 degrees flexion, shown in FIG. 14c, both the center of curvature O of posterior femoral condyles 20 and 22 and the center of curvature O' of the inboard and outboard posterior portions of the tibial plateau bearing surfaces 62 and 64, and 62a and 64a, respectively, coincide. When this occurs, the outboard portions 20b and 22b of the medial and lateral posterior femoral condyles 20 and 22 commence to function as cam member surfaces, and "link-up" and come into congruent contact with the outboard posterior portion of the tibial plateau arcuate bearing surfaces 62a and 64a. Concurrently, the inboard portion of the medial and lateral posterior femoral condyles 20a and 22a come into congruent contact with the respective inboard posterior portion of the tibial plateau bearing surfaces 62 and 64. At this point in the flexion range (approximately 30 degrees flexion), the congruent articular bearing contact area of the femoro-tibial joint (indicated as empty triangles in FIG. 14c) and the congruent contact area of the cam/follower mechanism, e.g. the outboard portion 20b and 22b of the posterior femoral condyles 20 and 22 contacting the outboard posterior portion of the tibial plateau bearing surfaces 62a and 64a (indicated as solid triangles in FIG. 14c), are equal in magnitude.

As the flexion angle increases (FIG. 14d) the articular bearing contact area of the femoro-tibial joint (indicated as empty triangles) remains constant. The articular contact area of the cam/follower mechanism increases proportionally with the flexion angle, since, the outboard portion 20b and 22b of the medial and lateral posterior femoral condyles 20 and 22 contacts both the outboard posterior portion of the tibial plateau bearing surfaces 62a and 64a and also the concave arcuate follower members 78 (indicated as solid triangles in FIG. 14d). The resulting articular bearing contact area of the cam/follower mechanism increases proportionally with the flexion angle to approximately 55 degrees flexion, where maximum bearing area is attained. This maximum articular contact area for knee components of intermediate size is equivalent to that of a 32 mm femoral (hip) head. From this point in the flexion range to maximum flexion the articular contact area of the cam/follower mechanism remains at a constant value—at the maximum level—as indicated as the solid triangles in FIGS. 14d and 14e.

From approximately 30 degrees flexion to full flexion the radius of curvature R and center of curvature O of the inboard portions 20a and 22a and outboard portions 20b and 22b of the medial and lateral posterior femoral condyles 20 and 22 are identical and coincident to the radius of curvature R and center of curvature O' of the outboard posterior portions of the tibial plateau bearing surfaces 62a and 64a, inboard posterior portions of the tibial plateau bearing surfaces 62 and 64, and concave arcuate follower member surfaces 78. The resulting articular bearing contact area of the cam/follower mechanism (indicated as solid triangles in FIGS. 14c through 14e), therefore, compliments and augments the articular contact area of the femoro-tibial joint (indicated as empty triangles in FIGS. 14c through 14e) from approximately 30 degrees flexion—where posterior rollback is completed—to full flexion. In this manner the cam/follower mechanism of the present invention (a.) provides posterior stabilization over the entire flexion range in surgical situations requiring either retention or sacrifice of the posterior (and anterior) cruciate ligament structures; and (b.) can provide significant articular bearing surface area augmentation to the articular surfaces of the femoro-tibial joint to sustain, distribute and transfer the imposed knee joint reaction forces within the flexion range from approximately 30 degrees flexion to full flexion.

Preferably and as shown in FIGS. 8a–8c, the tibial component 14 is comprised of a UHMWPE tibial plateau bearing component or insert 57, which is assembled and interlocked onto the metallic alloy tibial base component 84, via peripheral and centrally positioned engaging dovetail channels 83a and 83, and securely wedged and locked into final seated position with locking screw 93 incorporating an external thread 87a, which is installed anteriorly through posteriorly inclined clearance hole 75 and engages threaded port 87 located at the locking wedge portion 85 of tibial base component 84. The underside surface 86 of tibial base component 84 may incorporate a metallurgically integral sintered, diffusion bonded or plasma sprayed metallic alloy porous surface structure 88 (shown in partial section in FIG. 12) as a cemented or as a biological ingrowth bone fixation means.

The tibial base component 84 may incorporate short integral peg stabilizers 90 and an intramedullary stem 91 for augmentation of torsional and translational bone/prosthesis fixational constraint. Intramedullary stem 91 incorporates medial and lateral fixation stabilizing gussets 92 and a distal internal screw thread 88 (FIG. 2), which is oriented at posteriorly inclined angle 95 of approximately 3–5 degrees to more appropriately comply with the physiological medullary canal angulation of the tibial bone. The internal distal screw thread 88 within the intramedullary stem 91 allows assembly via mating external screw thread 88a of plug component 89 or similarly, the assembly of an intermedullary stem extension (not shown) of up to 15 mm or more diameter and up to 300 mm or more in length, if additional component stability is surgically indicated.

As still yet another principal embodiment of the present invention, the relatively large congruent bearing surface area of the cam/follower stabilizer mechanism and of the femoro-tibial joint, as described, advances the technical feasibility of employing ceramic-ceramic or metal-metal or ceramic-metal articular bearing material couples in the design of knee prostheses to minimize potential effects of in-situ generated wear surface particulates on bone morphology—recently associated with the metal/UHMWPE articular material couple in both hip and knee joint prostheses. Therefore, it may now become more feasible to manufacture the femoral component 12 and tibial plateau bearing component 57 of more rigid and wear resistant bearing materials, an approach which has not yet proven clinically feasible, relative to conventional knee prosthesis designs that generally employ "line" contact and associated high contact stress articular bearing geometry.

It will be appreciated that various changes or modifications can be incorporated into the present invention as claimed. For example, porous surface 56 on bone apposition surfaces 40, 42, 44, 46, 48, 50, 52 and 54 of femoral component 12 and porous surface 88 on bone apposition surface 86 of the tibial base component 84 can be prepared with a hydroxyapatite ceramic coating for improved bone attachment fixation, or an intramedullary stem can be added to the femoral component 12 for improved fixation stability, etc.

In accordance with a further aspect of the invention, prosthesis 10 may be modified to facilitate rotation of the bones of the knee joint in two planes, and in particular, the rotation of the tibia in the plane of its long axis. Generally, this capability is accomplished by the modification of the tibial component to cooperate with a flanged sleeve at the proximal insertion end thereof, which sleeve is fixed within the surgically prepared tibial end. Such constructions and their variants are shown in U.S. Pat. No. 4,136,405 to Pastrick et al. and U.S. Pat. No. 4,219,893 to Noiles, and the disclosures of these references are accordingly incorporated herein by reference for such purpose. The exact construction of this rotation means may vary in accordance with the teachings of the referenced patents, so that the present tibial component may be suitably modified in this fashion.

As stated earlier, the invention extends to the preparation of total knee prostheses with the inclusion of a hinged attachment. This embodiment will be described in detail hereinbelow and with reference to FIGS. 15–33, wherein like parts have been given like number designations advanced by 100 or 200, as the case may be.

Referring now to FIGS. 15–33, a mechanically linked variable-axis total knee prosthesis 110 according to this embodiment of the invention includes a metallic alloy femoral component 112, a corresponding tibial component 114 and interconnecting hinge pin 115. Femoral component 112 incorporates multi-radius medial and lateral condylar runners or condyles 116 and 118, that essentially mimic the shape of the natural femoral condyles of the distal femur which they replace.

Specifically, medial and lateral femoral condyles 116 and 118 include three distinct portions, that is, medial and lateral posterior condyle portions 120 and 122, respective distal femoral condyle portions 124 and 126 and respective anterior femoral condyle portions 128 and 130. The medial and lateral distal femoral condyles 124 and 126 comprise respective inboard distal femoral condyles 124a and 126a, and respective outboard cam member means 132. Medial and lateral cam member means 132 consist of anterior concave surface portion 132b and posterior convex cam member portion 132a. The medial and lateral posterior femoral condyles 120 and 122 consist of medial and lateral inboard portions 120a and 122a, and medial and lateral outboard portions 120b and 122b, respectively. The surface geometry of inboard portions 120a and 122a and outboard portions 120b and 122b of respective posterior femoral condyles 120 and 122 are continuous and have the same radius of curvature R and center of curvature O (FIGS. 20 and 28a).

Medial and lateral posterior femoral condyles, or femoral hinge components 120 and 122 incorporate a hinge passageway or transverse through port, 115b and 115a respectively, for insertion assembly of the hinge axis comprising hinge pin 115. An undercut locking groove 115c (FIG. 17) located concentrically within through port 115b in medial posterior femoral condyle 120 and positioned adjacent to the medial edge accepts locking ridge 195 for securing and locking of hinge pin 115 therein. The center-axis location of medial transverse port 115b and of lateral transverse port 115a is coincident with center of curvature O of the medial and lateral femoral condyles 120 and 122. It is understood that the undercut locking groove 115c can also be incorporated within lateral transverse port 115a of lateral posterior femoral condyle 122 or within both transverse ports, as well.

In addition, femoral component 112 includes medial and lateral cam member means 132, integrally positioned within the outboard portion of the medial and lateral distal femoral condyles 124 and 126, between the respective anterior femoral condyles 128 and 130 and posterior femoral condyles 120 and 122 of medial and lateral femoral condyles 116 and 118. As shown in the first embodiment of FIGS. 15–27, medial and lateral cam member means 132 are formed in two parts; the anterior concave portion 132b and the posterior convex cam surface portion 132a, each integral and continuous within the outboard portion of medial and lateral distal femoral condyles 124 and 126. Further, the radius of curvature R of medial and lateral convex cam surface portions 132a is identical to the radius of curvature R of medial and lateral posterior femoral condyles 120 and 122, the radius of curvature R of outboard (anterior to line 182) medial and lateral concave arcuate follower member means 178, the radius of curvature R of outboard portion of medial and lateral posterior tibial plateau bearing surfaces 162a and 164a, and the radius of curvature R of inboard portion of medial and lateral posterior tibial plateau bearing surfaces 162 and 164, with the respective centers of curvature located at points O and O', as shown in FIGS. 20, 23c and 28a.

The anterior portion of femoral component 112 is formed of the aforementioned anterior condyle portions 128 and 130 of medial and lateral condyles 116 and 118 and anterior patellar flange 136 integral with and interconnecting anterior condyle portions 128 and 130. The patella member 194 (not shown) articulates with the anterior patellar flange 136, biased laterally, at the outset of flexion and gradually transfers articulation in a natural-like manner to the distal aspects of anterior patellar flange 136 and anterior condyles 128 and 130 at approximately 25–30 degrees flexion.

The patella-femoral joint articulation then progresses to the inside corners 138 (FIGS. 19 and 22) of inboard distal femoral condyle portions 124a and 126a, traversing posteriorly, as the flexion angle increases to full range. It is noted that the proximal fixation surfaces of femoral component 112, which interface directly with bone in the biological fixation mode or with an interpositional thickness of polymethylmethacrylate (PMMA) bone cement in the cemented fixation mode, are the anterior surface 140, the medial and lateral anterior-distal surfaces 142a and 142, the medial and lateral distal surfaces 144 and 146, the medial and lateral distal-posterior surfaces 152 and 154 and also medial and lateral side-walls 125 and 127 and exterior roof 131 of intercondylar housing 137. These fixation surfaces may metallurgically incorporate an integral sintered, diffusion bonded or plasma sprayed porous surface structure 156, only a portion of which is shown in FIGS. 15, 17, 18, 19 and 21, as a femoral component 112 biological or cemented fixation means. In addition upwardly extending (Morse) tapered intramedullary stem 139, integral with exterior roof 131 of intercondylar housing 137, inserts into an appropriately prepared hole within the axial centerline portion of the distal femur bone to provide additional translational and varus-valgus rotational fixation stability. An intramedullary stem extension (not shown) can be added as a modular assembly, when additional component fixation is surgically indicated, and is attached and locked onto the Morse taper surface geometry of integral intramedullary stem 139.

Further, the centrally positioned intercondylar housing 137 interconnects the lateral aspect of medial femoral condyle 116 and the medial aspect of lateral femoral condyle 118. Housing 137 is formed externally by medial and lateral side-walls 125 and 127 and roof portion 131 which function as fixation surfaces, and is formed internally by medial and lateral intercondylar opening side-walls 116a and 116b and interior roof portion 129 which function as articular bearing surfaces—engaging exterior bearing surfaces 174a, 174b, 174c and 174d of upwardly extending tibial post 174 of tibial plateau bearing component 157.

The tibial plateau bearing component 157 includes inboard concave multi-radius medial and lateral tibial plateau bearing surfaces 158 and 160 which receive the inboard portions of convex multi-radius medial and lateral femoral condyles 116 and 118 consisting of inboard distal portions of anterior femoral condyles 128 and 130, inboard distal femoral condyles 124a and 126a and inboard portions 120a and 122a of posterior femoral condyles 120 and 122 for articulation thereon. In like manner it will be appreciated that the concave multi-radius shape of the inboard medial and lateral tibial plateau bearing surfaces 158 and 160 include anterior portions 170 and 172, central portions 166 and 168 and posterior portions 162 and 164, respectively. Between inboard medial and lateral tibial plateau bearing surfaces 158 and 160, the tibial plateau bearing component 157 incorporates an interconnecting, centrally positioned, anterior-posterior traversing and upwardly extending tibial post 174. A slotted hole 115d within tibial post 174 (FIG. 23c), located at an identical center-axis level as medial and lateral transverse through ports 115b and 115c within medial and lateral posterior condyles 120 and 122, accepts hinge pin 115, thus constituting a (hinge axis) rotational and A-P translational bearing surface member and mechanical linkage mechanism, interconnecting femoral component 112 and tibial component 114. The diameter of slotted hole 115c is equal to the diameter of hinge pin 115, plus appropriate diametral clearance. The length of slotted hole 115c is defined anteriorly by center-axis position O, the center of curvature of medial and lateral posterior femoral condyles 120 and 122 and of hinge pin 115; and posteriorly by center-axis position O', the center of curvature of medial and lateral concave arcuate follower member portions 178, the center of curvature of medial and lateral outboard and inboard portions of posterior tibial plateau bearing surfaces 162a and 164a, and 162 and 164, respectively, and center of curvature of articular surface 174a of tibial post 174.

During the early stages of flexion, medial and lateral sidewall surfaces 174d of tibial post 174 are positioned between respective inside corners 138 and sidewall surfaces 116a and 116b of intercondylar housing 137, adjacent to respective inboard distal condyle portions 124a and 126a of medial and lateral femoral condyles 116 and 118, as shown best in FIGS. 15, 17 and 18; providing semi-constrained medial-lateral and varus-valgus rotational freedom. The extent of translational and rotational freedom is a function of the dimensional clearances between the opposing surfaces.

Figures 30A, 30B, 30C:
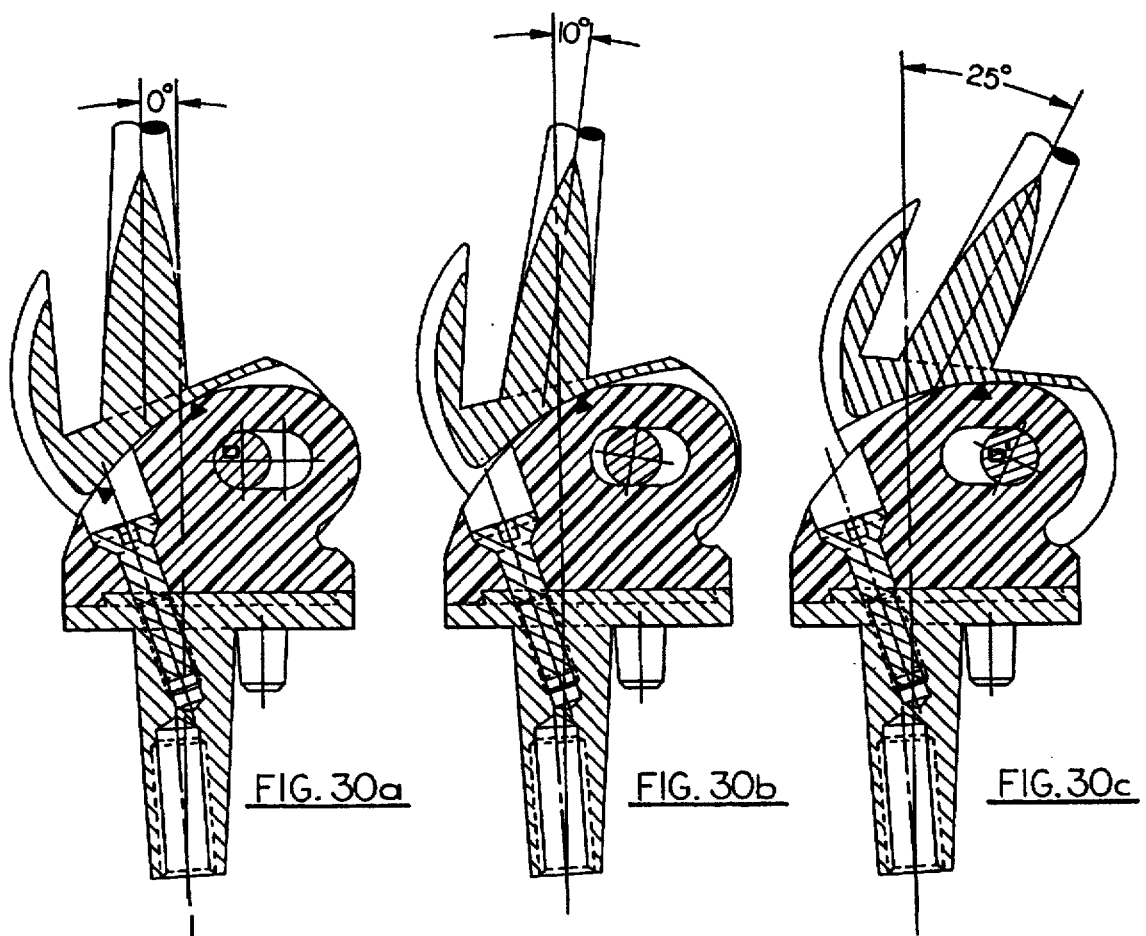
FIGS. 30a–30e are sectional views of the total knee prosthesis shown in FIG. 15 through center Section C—C, where the articular mechanics of hinge pin 115 within slotted hole 115d and of the central cam/follower mechanism—consisting of the interior slightly concave surface portion 129 of intercondylar housing 137 with the contacting exterior surfaces 174a, 174b and 174c of upwardly extending tibial post 174—are depicted at identical functional positions as in FIGS. 28a–28e and 29a–29e and where the extent of central cam/follower bearing contact area being indicated by the A–P contact length or traversing contact points, as shown by solid triangles with the anterior aspect being to the left and posterior to the right.
Figures 30D, 30E:
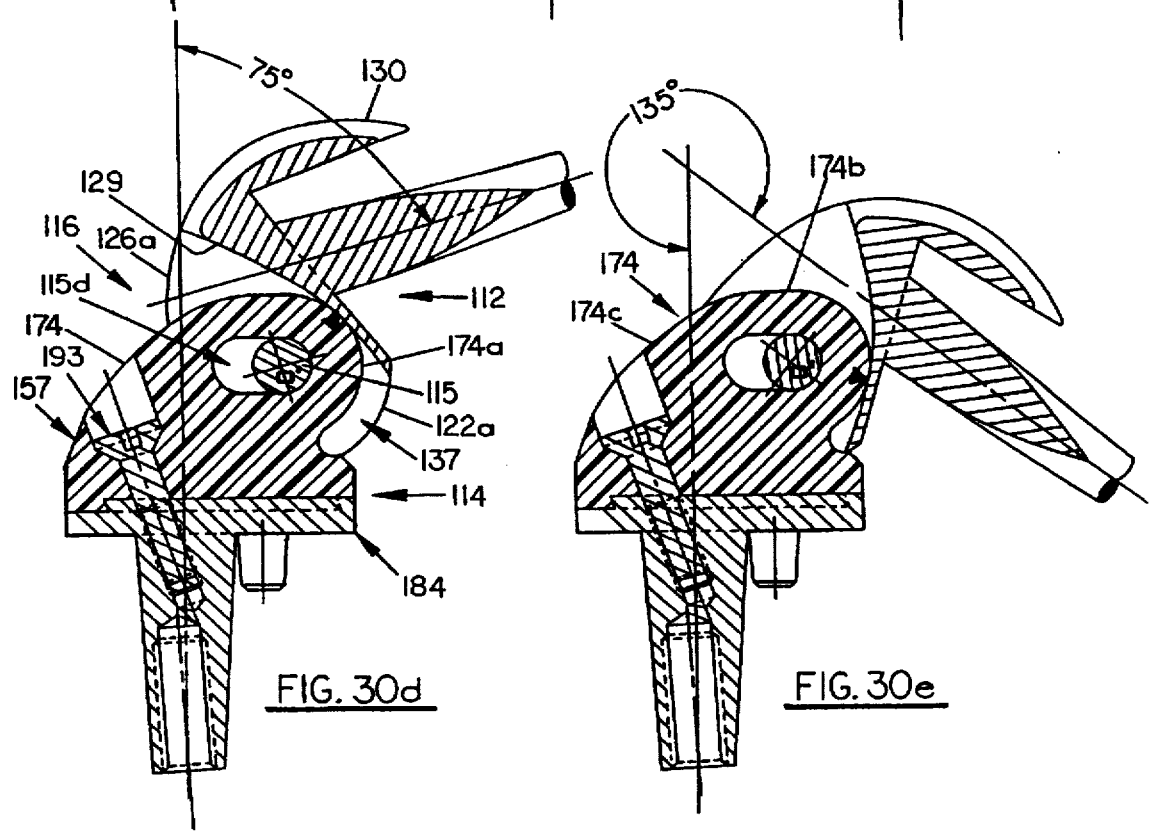

In addition at the outset of knee flexion, surface 174c of tibial post 174 contacts the anterior aspect of interior roof 129 of intercondylar housing 137, as best shown in FIG. 30a, and thereby functions as a mechanical stop or constraint to hyperextension (return) motion of the knee joint, and also provides broad bearing contact area to complement the bearing contact surfaces of the inboard femoro-tibial joint and outboard cam/follower members. Similarly, at the outset of flexion, medial and lateral anterior convex surface portions 178a of follower member means 176 contact respective concave surface portions 132b of cam member means 132, also functioning as a mechanical hyperextension stop and complementary bearing contact surface. Also at this time, hinge pin 115 is positioned within the anterior portion of slotted hole 115d of tibial post 174 at center-axis O, as shown in FIGS. 28a and 30a.

As the flexion angle increases beyond zero degrees, the articular interface between the tibial post/intercondylar housing bearing surfaces traverses posteriorly along surface 129. The initial coupling takes place with the anterior surface 174c, then with surface 174b and finally with posterior surface 174a of tibial post 174, as shown in FIGS. 30a through 30e. In the subsequent return or extension phase of knee motion the exterior bearing surface portions 174a, 174b and 174c of tibial post 174 with interior roof surface 129 of intercondylar housing 137 function as a (centrally positioned) cam/follower mechanism, providing smooth retracement of femoro-tibial articular mechanics, as in the flexion phase.

At the outset of knee flexion, the distal aspect of the anterior femoral condyles 128 and 130, and the anterior aspect of the inboard medial and lateral distal femoral condyles 124a and 126a of medial and lateral condyles 116 and 118, congruently contact the anterior portions 170 and 172 of inboard medial and lateral tibial plateau bearing surfaces 158 and 160, respectively. Also at this time, the anterior concave surface portion 132b of medial and lateral cam members 132 congruently contacts the anterior convex portion 178a of medial and lateral follower members 176, respectively, as best shown in FIGS. 16 and 28a—with both articular member surfaces providing both posterior (tibia-to-femur) and anterior (femur-to-tibia) stabilization of the extended or 0 degree flexed knee joint.

Tibial plateau bearing component 157 includes outboard medial and lateral follower member means 176 consisting of respective anterior convex surface 178a, central concave arcuate follower member surface means 178 extending anterior of mid-line 182, and outboard portion of posterior concave arcuate tibial-plateau bearing surfaces 162a and 164a extending posterior of mid-line 182. The medial and lateral cam member means 132 within respective distal femoral condyles 124 and 126 of femoral component 112 include an anterior concave surface portion 132b and a posterior convex cam portion 132a. After posterior rollback is completed at approximately 25-30 degrees flexion to full flexion, the cam member function is transferred to the outboard portion 120b and 122b of the medial and lateral posterior femoral condyles 120 and 122, respectively. It will be appreciated that the medial and lateral concave arcuate follower member portion 178 of tibial plateau bearing component 157, the respective outboard portions of the posterior tibial plateau bearing surfaces 162a and 164a and inboard portions of the posterior tibial plateau bearing surfaces 162 and 164 are defined by the identical radius of curvature R with a common center of curvature located at point O', as shown in FIG. 23c. It will be further appreciated that the convex cam member portion 132a of medial and lateral cam members 132 is also defined by radius of curvature R centered at O', as shown in FIG. 28a. Whereas, the radius of curvature R of medial and lateral inboard portions 120a and 122a and respective outboard portions 120b and 122b of medial and lateral posterior femoral condyles 120 and 122 is also equal to R, but with the center of curvature located at point O—as is best shown in FIG. 20 and 28a.

Figures 29A, 29B, 29C:
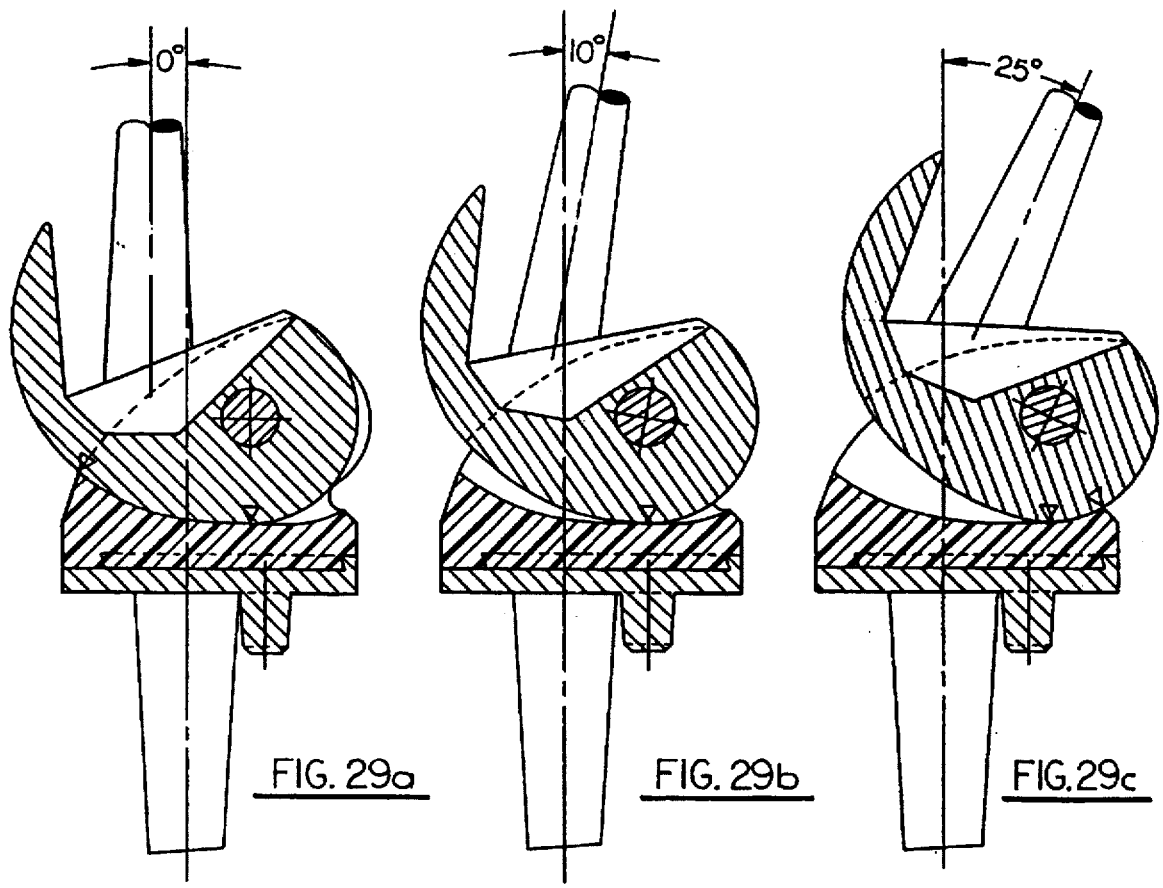
FIGS. 29a–29e are (mirror image) sectional views of the total knee prosthesis shown in FIG. 15 through Section B—B, where the articular mechanics of the inboard lateral (and medial) femoro-tibial joint are depicted at coincident functional positions as in FIGS. 28a–28e and where the extent of femoro-tibial contact area being indicated by the A–P contact length, as shown by empty triangles with the anterior aspect being to the left and posterior to the right.
Figures 29D, 29E:
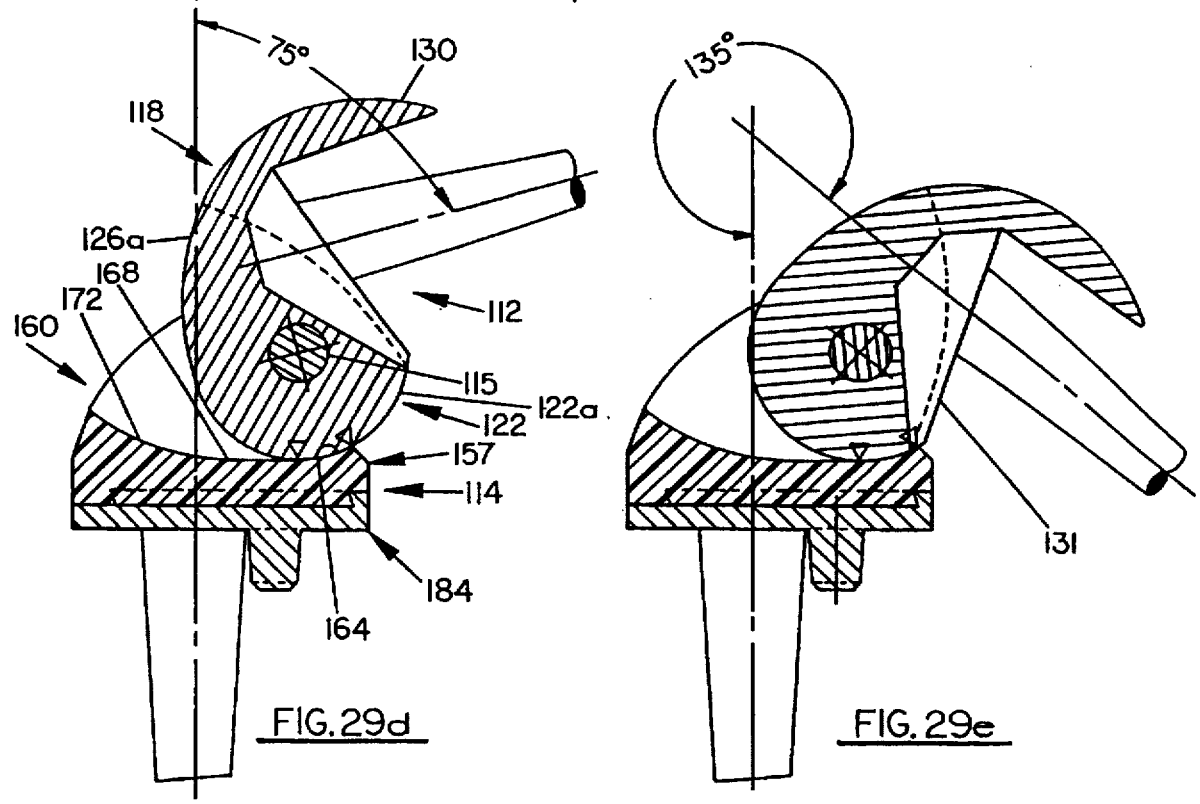

Relative to the mechanics of the outboard cam/follower member means 132, at the outset of knee flexion the anterior concave cam member portion 132b and anterior convex follower surface portion 178a come into congruent contact and the anterior face of convex cam member portion 132a of medial and lateral cam member means 132 congruently contacts the concave arcuate follower member portion 178, anterior of the mid-line 182, as shown best in FIGS. 28a and 29a. This contact state between medial and lateral cam member portions 132b and 132a and respective follower member portions 178a and 178, represents the earliest stage of posterior (tibia-to-femur) stabilization. As flexion angle increases (FIG. 28b), the camming action between the ensuing non-congruent contact of the convex cam member portions 132a of medial and lateral cam members 132 and upward sloping concave arcuate follower member portions 178 of medial and lateral follower members 176, causes the center of curvature O of the medial and lateral posterior condyles 120 and 122 of femoral component 112 and of assembled hinge pin 115 to displace posteriorly, approaching center-axis O' of slotted hole 115c and coincident center of curvature O' of concave arcuate follower member portions 178, center of curvature O' of outboard portion of posterior tibial plateau bearing surfaces 162a and 164a and center of curvature O' of inboard portion of posterior tibial plateau bearing surfaces 162 and 164; therefore, allowing the inboard medial and lateral distal femoral condyles 124a and 126a of femoral component 112 to posteriorly translate or roll back, relative to the inboard medial and lateral tibial plateau bearing surfaces 158 and 160 of tibial plateau bearing component 157.

Posterior rollback of the inboard femoro-tibial joint is concluded at approximately 25–30 degrees flexion. As best shown in FIGS. 28c and 29c, both the center of curvature O of posterior femoral condyles 120 and 122 and the center of curvature O' of the inboard and outboard portions of posterior tibial plateau bearing surfaces (162 and 164) and (162a and 164a), respectively, coincide. When this occurs, the outboard portions 120b and 122b of medial and lateral posterior femoral condyles 120 and 122 come into congruent contact with the outboard portion of posterior tibial plateau arcuate bearing surfaces 162a and 164a, as shown in FIG. 28c.

Coincidentally, the inboard portions of the medial and lateral posterior femoral condyles 120a and 122a come into congruent contact with the respective inboard portion of posterior tibial plateau bearing surfaces 162 and 164, as shown in FIG. 29c. At this point in the flexion range (approximately 25–30 degrees flexion), the extent of the resulting bearing contact area (contact length) of the femoro-tibial joint is indicated by the empty triangles in FIG. 29c and similarly, the extent of the resulting bearing contact area of the cam/follower mechanism, e.g. the outboard portion 120b and 122b of the posterior femoral condyles 120 and 122 contacting the outboard portion of posterior tibial plateau bearing surfaces 162a and 164a is indicated by the solid triangles in FIG. 28c.

As flexion angle increases from 25–30 degrees (FIG. 29c) to full flexion (FIG. 29e), the bearing contact area of the inboard femoro-tibial joint (indicated by the empty triangles) remains constant. The articular contact area of the outboard medial and lateral cam/follower mechanisms, however, increases proportionally with flexion angles above the 25–30 degree level (FIG. 28c), where the outboard portions 120b and 122b of medial and lateral posterior femoral condyles 120 and 122 maintain contact congruency with the respective outboard portions of posterior tibial plateau bearing surfaces 162a and 164a, while subsequently traversing anteriorly, contacting the respective concave arcuate follower members 178 in a proportional manner as the flexion angle increases. The resulting bearing contact area of the outboard medial and lateral cam/follower mechanisms, therefore, increases proportionally with the flexion angle from the 25–30 degree level (FIG. 28c) to approximately 75 degrees flexion (FIG. 28d), where maximum bearing contact area is attained. The magnitude of the resulting maximum contact area for knee components of intermediate size is equivalent to that of a 32 mm diameter (hip arthroplasty) femoral head. From this point in the flexion range to maximum flexion the bearing contact area of the outboard medial and lateral cam/follower mechanisms is maintained constant at the maximum level, as indicated by the solid triangles in FIGS. 28d and 28e.

After posterior femoro-tibial rollback at approximately 25–30 degrees flexion to full flexion, the radius of curvature R and center of curvature O of the inboard portions 120a and 122a and outboard portions 120b and 122b of medial and lateral posterior femoral condyles 120 and 122 are identical and coincident with the radius of curvature R and center of curvature O' of the outboard portions of respective posterior tibial plateau bearing surfaces 162a and 164a, of inboard portions of respective posterior tibial plateau bearing surfaces 162 and 164 and of respective outboard concave arcuate follower member surfaces 178, as shown in FIGS. 23c and 28c. The resulting bearing contact area of the outboard medial and lateral cam/follower mechanisms (indicated by the solid triangles in FIGS. 28a through 28e), the bearing contact area of the central cam/follower mechanism (indicated by the solid triangles in FIGS. 30a through 30e) and the mechanical linkage bearing of hinge pin 115 within slotted hole 115d (FIGS. 30a through 30e), therefore by design, compliment and augment the bearing contact area of the femoro-tibial joint (indicated by the empty triangles in FIGS. 29a through 29e) to sustain, transfer and distribute the imposed knee joint reaction forces from the outset of knee flexion and throughout the full flexion range.

Preferably, as shown in FIGS. 23a–23c, the tibial component 114 is comprised of UHMWPE (ultra-high molecular weight polyethylene) tibial plateau bearing component 157, which is assembled and interlocked onto metallic alloy tibial base component 184 via side-posterior peripheral and central engaging dovetail channels 183a and 183, respectively. In this manner the tibial plateau bearing component 157 is securely wedged and locked into final seated position by locking screw 193, which is installed anteriorly through anteriorly inclined clearance hole 175 allowing screw thread 187a to engage threaded port 187, located within central wedge portion 185 of tibial base component 184. The underside surface 186 of tibial base component 184 may incorporate a metallurgically integral sintered, diffusion bonded or plasma sprayed metallic alloy porous surface structure 188 (shown in partial section in FIG. 27) as a cemented or biological bone ingrowth fixation means. The tibial base component 184 may incorporate short integral peg stabilizers 190 and intramedullary stem 191 for improved prosthesis fixational considerations. Intramedullary stem 191 incorporates medial and lateral fixation stabilizing gussets 192 and distal internal screw thread 188, which is oriented at an anteriorly inclined angle 194 of approximately 3–5 degrees to more appropriately comply with the physiological medullary canal orientation of the tibial bone. The internal distal screw thread 188 within intramedullary stem 191 allows assembly, via mating external screw thread 188a, of stem plug component 189 or assembly of an intermedullary stem extension (not shown) of 15 mm or more diameter and 300 mm or more in length, if additional tibial component stability is surgically indicated.

As still yet another principal embodiment of the present invention, the relatively large congruent bearing contact surfaces of the outboard cam/follower mechanism, of the femoro-tibial joint and of the hinge pin/tibial post connection, as described, increases the technical feasibility of employing ceramic-ceramic or metal-metal or ceramic-metal articular bearing material couples to minimize potential adverse effects of in-situ generated particulate wear debris on bone morphology—recently associated with the metal/UHMWPE articular bearing couple in both hip and knee joint prostheses. Therefore, it may now become more feasible to manufacture the femoral component 112 and tibial plateau bearing component 157 of more rigid and more wear resistant bearing materials, an approach which has not yet proven clinically feasible, relative to conventional knee prosthesis designs, which generally employ "line" contact and associated high contact stress articular bearing geometries.

It will be appreciated that various changes or modifications can be incorporated into the present invention as claimed. For example porous surface 156 on fixation surfaces 140, 142, 142a, 144, 146, 152 and 154 of femoral component 112 and porous surface 188 on fixation surface 186 of the tibial base component 184 can be prepared with a hydroxyapatite ceramic coating for improved biological bone ingrowth fixation. Also, tibial bearing component 174 and engaging tibial base component 184 can be designed according to known and clinically used methods (reference U.S. Pat. No. 4,136,405 to Pastrick et al and U.S. Pat. No. 4,219,893 to Noiles), which employ a rotating platform to allow semi-constrained or unconstrained femoro-tibial axial rotational motion of the reconstructed knee joint.

The present variable-axis mechanically linked total knee prosthesis invention can also be readily modified to reflect a more conventional design, e.g. a uni-axis hinged-type total knee prosthesis, as shown in FIGS. 31 and 32. The numerical identification of similar constituent parts is consistent with FIGS. 15–27, however, is advanced by a numerical factor of 100.

The femoral component 212 of the uni-axis mechanically linked total knee prosthesis 214 is essentially similar in design to femoral component 112 of the variable-axis mechanically linked total knee prosthesis 114. Hinge pin 215 is identical to hinge pin 115 relative to location, functionality and method of retention within medial and lateral femoral condyles 220 and 222; however, its relative femoro-tibial position is fixed throughout the flexion range. Upwardly extending tibial post 274 remains centrally positioned and bounded between the lateral side 216b of medial femoral condyle 216 and the medial side 216a of lateral femoral condyle 218 with exterior surfaces 274a, 274c and 274d respectively contacting interior roof surface 229 and surfaces 216a and 216b of intercondylar housing 237.

The principal design difference of tibial post 274, compared to tibial post 174, is the incorporation of a cylindrical transverse hinge pin hole 215c rather than the slotted hole 115c of the previous design; thus, functioning as a uni-axis bearing rather than a variable-axis bearing. The center axis of transverse hole 215c is coincident with center of curvature O of medial and lateral posterior femoral condyles 220 and 222, center of curvature O of medial and lateral outboard concave arcuate member portions 278 and center of curvature O of outboard and inboard portions of posterior tibial plateau bearing surfaces (262a and 264a) and (262 and 264), as shown in FIG. 31; with respective arcuate surface geometries defined by radius of curvature R at center of curvature O. The outboard concave surface portions 232b within the anterior aspect of medial and lateral distal femoral condyles 224 and 226, that contact respective convex surface portions 278a of tibial plateau bearing component 257, and anterior surface portion 274c of upwardly extending tibial post 274, that contacts anterior portion of interior roof 229 of intercondylar housing 237, function as mechanical stops or constraints, thereby limiting the extent of hyperextension of the knee joint.

The principal embodiment of the present mechanically linked uni-axis total knee prosthesis relates to the central intercondylar bearing member surfaces, being comprised of anterior outer surface 274c and central-posterior outer surface 274a of upwardly extending tibial post 274 articulating with interior roof surface 229 of intercondylar housing 237 of femoral component 212. This articulation takes place throughout the flexion-extension range in a manner which compliments the femoro-tibial joint bearing members being comprised of inboard portions 220a and 222a of medial and lateral posterior femoral condyles 220 and 222 articulating with respective inboard portions of posterior tibial plateau bearing surfaces 262 and 264 of tibial bearing component 257, and outboard portions 220b and 222b of medial and lateral posterior condyles 220 and 222 articulating with outboard portions of posterior tibial plateau bearing surfaces 262a and 264a and anterior arcuate surface portions 278 of tibial plateau bearing component 257. This articulation is best shown in FIGS. 33a–33c, which depicts a laterally directed sagittal sectional view of the uni-axis mechanically linked total knee prosthesis of FIG. 31 at the outset of flexion (FIG. 33a), at 25 degrees flexion (FIG. 33b) and at full flexion (FIG. 33c). The bearing contact length of the inboard femoro-tibial joint is indicated by the empty triangles, the contact length of the outboard femoro-tibial joint by the solid triangles and that of the central articular intercondylar surfaces by solid squares, which of course work concurrently and in conjunction with the hinge pin/tibial post journal bearing surface to sustain, transfer and distribute the applied joint reaction forces of the functional knee joint.

Having described specific preferred embodiments of the present invention with reference to the accompanying drawings, it will be appreciated that the present invention is not limited to those precise embodiments, and that various changes and modifications can be effected therein by one of ordinary skill in the art without departing from the spirit or scope of the invention as defined by the appended claims.

What is claimed is:

1. A total knee prosthesis capable of providing resurfacing to the adjacent ends of the existing bone structures, as well as total posterior stabilization to the knee joint, comprising:

a) a femoral component including:
i) a medial condyle having an anterior portion, a distal portion and a posterior portion;
ii) a lateral condyle having an anterior portion, a distal portion and a posterior portion;
iii) an anterior patellar flange interconnecting the anterior portions of the medial and lateral condyles in parallel, spaced apart relation; and
iv) cam member means integral with said medial and lateral condyles and located outboard thereof, said cam member means having an anteriorly located concave cam member surface and a posteriorly located convex cam member surface;

b) a tibial component including:
i) multi-radius tibial plateau bearing surface means for receiving said medial and lateral condyles for rolling and sliding movement thereon; and
ii) follower member means integral with said bearing surface means for receiving the cam surfaces of said cam member means for rotational and sliding movement thereon; and c) hinge means associated with and hingeably connecting said femoral component and said tibial component, said hinge means having a variable axis of rotation and enabling the rotational and sliding contact and anterior-posterior translation to take place between said femoral component and said tibial component;

d) the cam member surfaces of said cam member means being in contact with said follower member means for substantially the entire flexion range of the knee.

2. A total knee prosthesis according to claim 1, wherein said hinge means comprises plural spaced apart femoral hinge components, a tibial hinge component located between said femoral hinge components, and a hinge axis comprising a hinge pin extending therebetween.

3. A total knee prosthesis according to claim 2, wherein said hinge components define a hinge axis passageway for the reception of said hinge pin.

4. A total knee prosthesis according to claim 3, wherein the portion of said hinge axis passageway defined by said tibial hinge component comprises a slot.

5. A total knee prosthesis according to claim 4, wherein said hinge means defines a hinge-related posterior stabilization means including said slot and said hinge pin.

6. A total knee prosthesis according to claim 2, including locking means associated with said femoral hinge components for releasably retaining said hinge pin therein.

7. A total knee prosthesis according to any of claims 2–4, wherein said hinge means defines a hinge-related posterior stabilization means.

8. A total knee prosthesis according to claim 7, wherein said hinge-related posterior stabilization means comprises cam means defined by said tibial hinge component and follower means defined by said femoral hinge components.

9. A total knee prosthesis according to claim 8, wherein said cam means comprises said tibial hinge component, and said follower means comprises an intercondylar housing defined between said femoral hinge components and adapted to receive said tibial hinge component for articulating engagement therein.

10. A total knee prosthesis according to claim 9, wherein said tibial hinge component comprises a tibial post having opposed lateral peripheral surfaces and an upper peripheral surface; said intercondylar housing has lateral wall surfaces and a roof surface; and wherein respective lateral wall surfaces and lateral peripheral surfaces engage each other in sliding contact, and said roof surface and said upper peripheral surface engage each other in rolling and sliding contact.

11. A hinge assembly for use in a knee prosthesis adapted to provide hingeable connection between a femoral component and a tibial component of such knee prosthesis, to enable anterior-posterior translation to take place between said femoral component and said tibial component and to offer total posterior stabilization thereto, said hinge assembly comprising:

a) plural spaced apart femoral hinge components;

b) a tibial hinge component located between said femoral hinge components, said tibial hinge component comprising a tibial post having opposed lateral peripheral surfaces and an upper peripheral surface;

c) a hinge axis comprising a hinge pin extending between said femoral hinge components and said tibial hinge component; and d) hinge-related posterior stabilization means comprising cam means comprising said tibial hinge component and follower means defined by said femoral hinge components, said follower means comprising an intercondylar housing defined between said femoral hinge components and adapted to receive said tibial hinge component for articulating engagement therein, and wherein said intercondylar housing has lateral wall surfaces and a roof surface; and wherein respective lateral wall surfaces and lateral peripheral surfaces engage each other in sliding contact, and said roof surface and said upper peripheral surface engage each other in rolling and sliding contact.

12. A hinge assembly according to claim 11, wherein said hinge components define a hinge axis passageway for the reception of said hinge pin.

13. A hinge assembly according to claim 12, wherein the portion of said hinge axis passageway defined by said tibial hinge component comprises a slot.

14. A hinge assembly according to claim 13, wherein said posterior stabilization means includes said slot and said hinge pin.

15. A hinge assembly according to claim 13 wherein said slot is adapted to be oriented with its longitudinal dimension in a horizontal plane when said hinge assembly is installed and in use.

16. A hinge assembly according to claim 11, including locking means associated with said femoral hinge components for releasably retaining said hinge pin therein.

* * * * *